United States Patent
Blum et al.

(10) Patent No.: US 11,471,553 B2
(45) Date of Patent: *Oct. 18, 2022

(54) EXHALED AIR PURIFICATION UNIT AND SYSTEM FOR INDOOR MULTI-PERSON VENUES OR ENVIRONMENTS

(71) Applicant: Air-Clenz Systems, LLC, Atlanta, GA (US)

(72) Inventors: Ronald Blum, Atlanta, GA (US); Anita Broach, Christiansburg, VA (US); Russell French, Atlanta, GA (US)

(73) Assignee: Air-Clenz Systems, LLC, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/722,981

(22) Filed: Apr. 18, 2022

(65) Prior Publication Data

US 2022/0233740 A1    Jul. 28, 2022

Related U.S. Application Data

(63) Continuation of application No. 17/300,936, filed on Dec. 15, 2021, and a continuation of application No. 17/404,570, filed on Aug. 17, 2021, and a continuation of application No. 17/353,341, filed on Jun. 21, 2021, and a continuation of application No.
(Continued)

(51) Int. Cl.
*B01D 46/00* (2022.01)
*A61L 9/20* (2006.01)
*B01D 46/46* (2006.01)
*A61L 9/14* (2006.01)
(Continued)

(52) U.S. Cl.
CPC .............. *A61L 9/20* (2013.01); *A61L 9/145* (2013.01); *A61L 9/16* (2013.01); *B01D 46/0028* (2013.01); *B01D 46/0043* (2013.01); *B01D 46/0049* (2013.01); *B01D 46/46* (2013.01); *A61L 2209/12* (2013.01); *A61L 2209/14* (2013.01); *A61L 2209/16* (2013.01); *B01D 2273/30* (2013.01); *B01D 2279/50* (2013.01); *B01D 2279/65* (2013.01); *B64D 13/06* (2013.01); *B64D 2013/0651* (2013.01)

(58) Field of Classification Search
CPC ... A61B 5/6893; A61B 5/0022; A61B 5/0823; A61B 5/4803; A61B 5/7246; A61B 5/7282; A61B 5/7264; A61B 2503/22; A61B 2560/0252; A61B 2560/025; A61B 2562/0204; A61B 2565/029; B60H 1/008; B60H 1/00742; B60H 3/02; B60H 3/06; G05B 2219/2614; G05B 2219/2637; A61L 9/22
USPC .......... 55/385.1, 472, 473, DIG. 34; 96/424, 96/397, 417, 422; 95/25, 26
See application file for complete search history.

(56) References Cited

U.S. PATENT DOCUMENTS 11,324,850 B2 *   5/2022   Blum ........................ A61L 9/16

FOREIGN PATENT DOCUMENTS

JP           2004-113561 A *   4/2004   .............. F24F 7/06

* cited by examiner

*Primary Examiner* — Minh Chau T Pham
(74) *Attorney, Agent, or Firm* — Woods Rogers PLC; Nathan A. Evans

(57) ABSTRACT

An air purification unit and/or system for an environment with multiple seated individuals, including an air collector and air purification chamber, to be used independently from or in conjunction with the environment's air handling system.

30 Claims, 29 Drawing Sheets

Related U.S. Application Data

17/331,239, filed on May 26, 2021, now Pat. No. 11,324,850.

(60) Provisional application No. 63/182,964, filed on May 2, 2021, provisional application No. 63/173,443, filed on Apr. 11, 2021, provisional application No. 63/158,983, filed on Mar. 10, 2021, provisional application No. 63/156,598, filed on Mar. 4, 2021, provisional application No. 63/149,581, filed on Feb. 15, 2021, provisional application No. 63/125,701, filed on Dec. 15, 2020, provisional application No. 63/063,727, filed on Aug. 10, 2020, provisional application No. 63/060,009, filed on Aug. 1, 2020, provisional application No. 63/051,309, filed on Jul. 13, 2020, provisional application No. 63/050,253, filed on Jul. 10, 2020, provisional application No. 63/048,877, filed on Jul. 7, 2020, provisional application No. 63/046,430, filed on Jun. 30, 2020, provisional application No. 63/031,321, filed on May 28, 2020, provisional application No. 63/029,956, filed on May 26, 2020.

(51) Int. Cl.
*A61L 9/16* (2006.01)
*B64D 13/06* (2006.01)

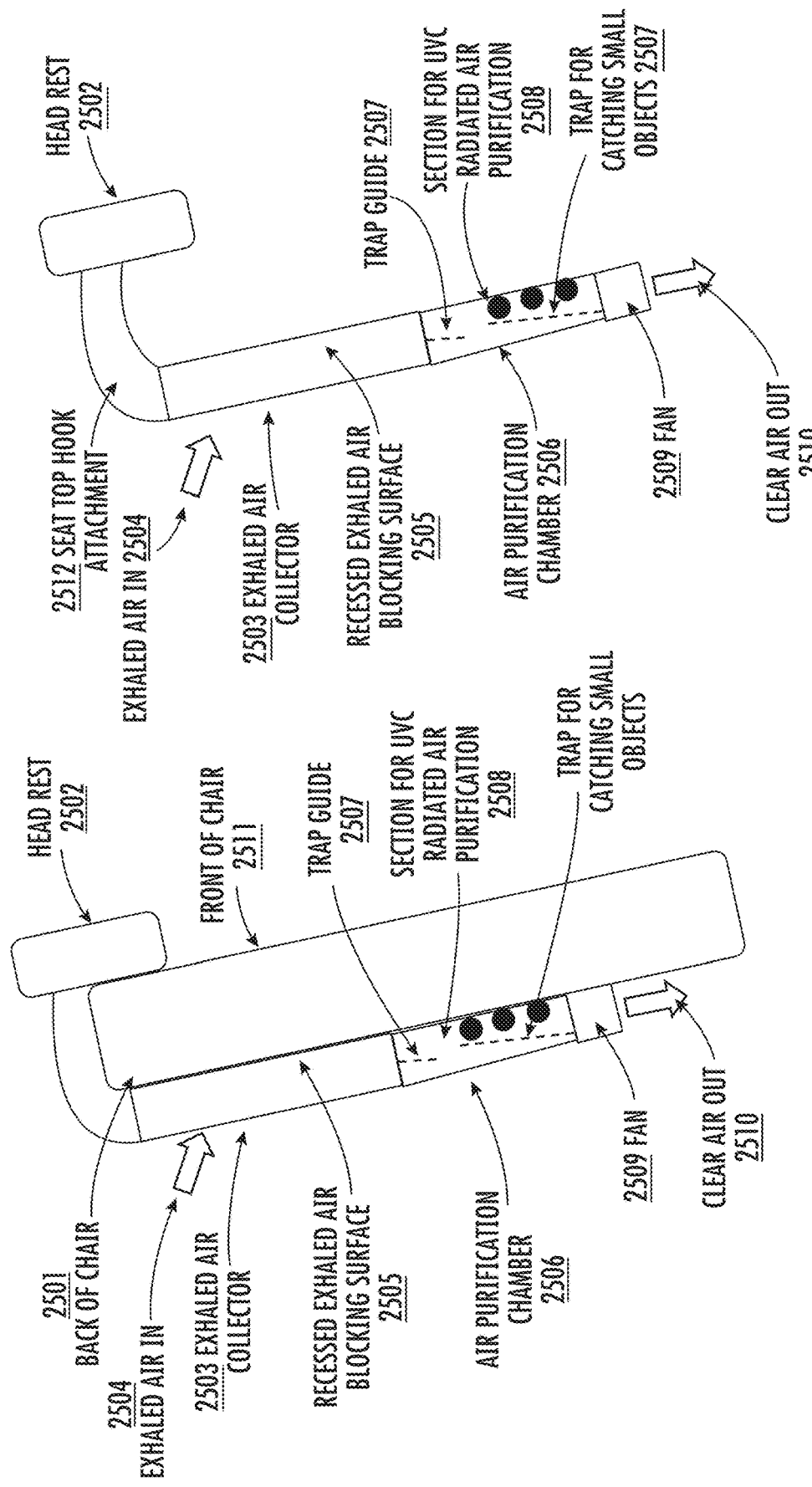

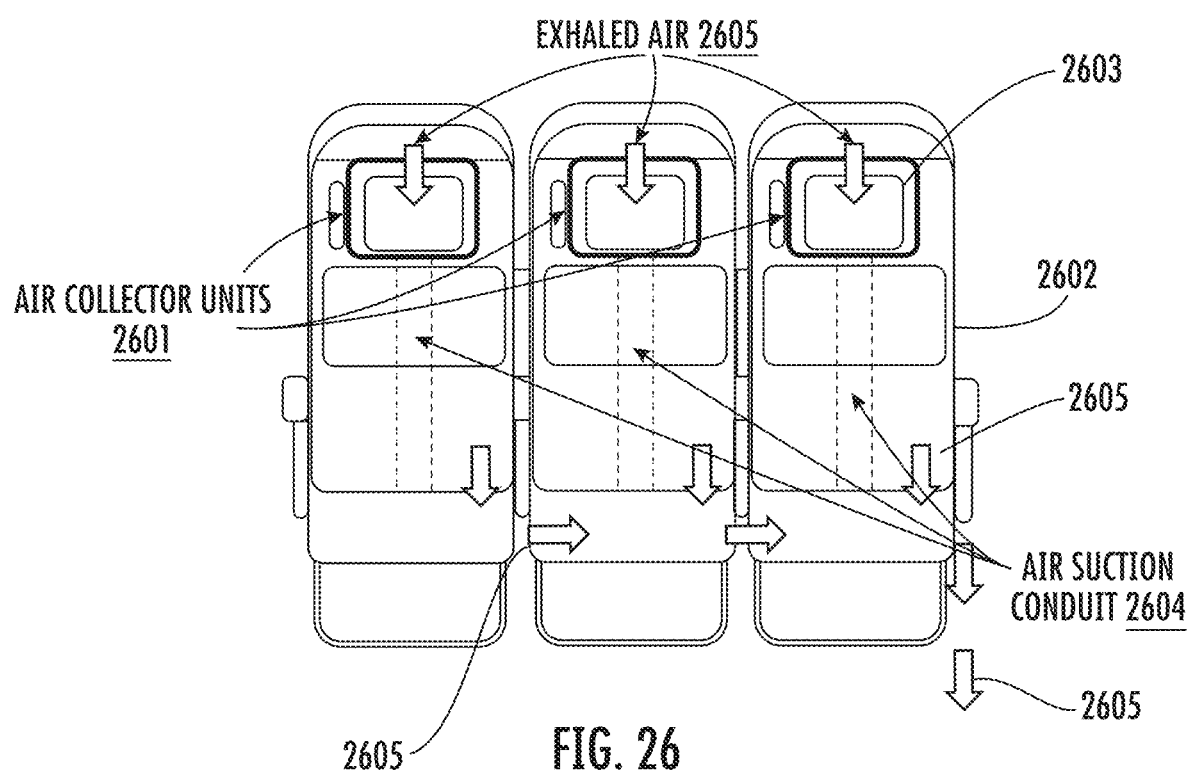

EXHALED AIR PURIFICATION UNIT AND SYSTEM FOR INDOOR MULTI-PERSON VENUES OR ENVIRONMENTS

CROSS-REFERENCE TO RELATED APPLICATIONS

The present application is a continuation of and relies on the disclosures of and claims priority to and the benefit of the filing date of U.S. application Ser. No. 17/331,239, filed May 26, 2021, now U.S. Pat. No. 11,324,850 B2, which relies on the disclosures of and claims priority to and the benefit of the filing dates of the following U.S. Provisional Patent Applications:

U.S. Appl. No. 63/029,956, Microbe Protection Systems, filed May 26, 2020;
U.S. Appl. No. 63/031,321, Microbe Protection Modules, filed May 28, 2020;
U.S. Appl. No. 63/046,430, Air Suction Sterilization Elevator Car, filed Jun. 30, 2020;
U.S. Appl. No. 63/048,877, Vehicle Microbe Protection System, filed Jul. 7, 2020;
U.S. Appl. No. 63/050,253, Advanced Air Suction Sterilization Elevator Car, filed Jul. 10, 2020;
U.S. Appl. No. 63/051,309, Advanced Vehicle Microbe Protection System, filed Jul. 13, 2020;
U.S. Appl. No. 63/060,009, Advanced Air Suction Air Sterilization Protection System, filed Aug. 1, 2020;
U.S. Appl. No. 63/063,727, Advanced Microbe Trap and Face Mask, filed Aug. 10, 2020;
U.S. Appl. No. 63/125,701, Advanced Air Purification System for Multi-Person Environment, filed Dec. 15, 2020;
U.S. Appl. No. 63/149,581, Multi-person Venue Air Purification System, filed Feb. 15, 2021;
U.S. Appl. No. 63/156,598, Air Handling Purification System, filed Mar. 4, 2021;
U.S. Appl. No. 63/158,983, Air Handling Purification System, filed Mar. 10, 2021;
U.S. Appl. No. 63/173,443, Recessed Personal Air Purifier for Backside of Seat Back, filed Apr. 11, 2021; and
U.S. Appl. No. 63/182,964, Personal Air Purification Unit and System, filed May 2, 2021.

The present application is a continuation of and relies on the disclosures of and claims priority to and the benefit of the filing date of U.S. application Ser. No. 17/353,341, filed Jun. 21, 2021.

The present application is a continuation of and relies on the disclosures of and claims priority to and the benefit of the filing date of U.S. application Ser. No. 17/404,570, filed Aug. 17, 2021.

The present application is a continuation of and relies on the disclosures of and claims priority to and the benefit of the filing date of U.S. application Ser. No. 17/300,936, filed Dec. 15, 2021.

The disclosures of all the above applications are hereby incorporated by reference herein in their entireties.

BACKGROUND

Field of the Invention

The present invention is directed to an air purification unit and/or system providing the ability to capture, isolate, transport, and/or destroy airborne pathogens and contaminants faster than currently available HVAC systems, HVAC purification systems, and/or HVAC air handling systems, permit. The present invention further includes the collection and analysis of an individual's exhaled air with the end point of identifying potential health abnormalities associated with the individual whose exhaled air was analyzed/screened.

Description of the Related Art

Aerosol spray which transports viruses, including coronavirus ("COVID"), occurs from a human exhaled breath, talking, shouting, coughing, and sneezing. The louder the noise the human makes with his or her voice, lungs, throat, or mouth generally the farther the viral or bacterial aerosol is moved in the air. Recent studies show that an aerosol comprising viral float can remain airborne for up to 15 minutes in a closed confined environment. Research studies have showed that singing, yelling, coughing, and sneezing can spread COVID aerosol up to 3+ meters. COVID 19, COVID variants, corona virus, measles, mumps, SARS, smallpox, common colds, influenza, and tuberculosis are examples of pathogens that can be spread by way of being airborne. Closed confined multi-seated indoor environments are extremely vulnerable to coronaviral spread. There is a need to provide a mechanism whereby individuals can safely be seated within such environments. This applies to all such multi-seated venues such as, by way of example only, vehicles (land, sea and air) (e.g., aircraft, airplanes, jets, boats, ships, cars, automobiles, trucks, trains, subways, buses, etc.), theaters (e.g., auditoriums, educational, sports, performing arts, cinema, etc.), and houses of worship (e.g., churches, synagogues, temples, etc.).

SUMMARY

The present invention relates to all types of multi-seated indoor environments or venues where one or more chairs, seats, or benches are positioned in front or behind one another. In one embodiment of the present invention, an air purification system is provided for all multi-seated indoor or enclosed venues, which includes an exhaled air collector that can be integral with a seat, attached to a seat, or located free standing, separated, and behind a seat. In other embodiments of the present invention, an air purification unit includes an air purification chamber combined with the exhaled air collector, which can also be integral with the seat, attached to the seat, or located free standing, separated, and behind the seat. In aspects, the air purification chamber can be remote from but connected to the exhaled air collector, such as connected by a conduit, or directly adjacent and attached thereto. In embodiments of the present invention, the conduit may include, by way of example only, a tube, corridor, channel, or tunnel-like structure. The conduit can be remote from the chair. The conduit can be one of: located within the chair, attached to the chair, or separated from the chair. The conduit can be comprised of any material, such as, by way of example only, plastic, metal, polymer, rubber, glass, or ceramics. The conduit can be an air suction conduit. The conduit can be that of the material of the chair that forms a tunnel or channel inside of or connected to a chair. The conduit can connect one or multiple exhaled air collectors to one or more remote air purification chambers, thereby creating a networked and connected air purification system. The conduit can connect the air purification chamber of an air purification unit to the air purification unit's exhaled air collector. The conduit can move exhaled air through or along a chair and towards the floor of a vehicle or aircraft cabin, in aspects.

In embodiments of the present invention, an air purification system may comprise a plurality of exhaled air collectors networked to one or more remote air purification chambers. An air purification unit may comprise an exhaled air collector and an air purification chamber.

As used herein an airborne particulate can be that of, but is not limited to, a virus, bacteria, fungus, pathogen, or contaminant. As used herein a pathogen can include bacteria, fungi, protozoa, worms, viruses, and even infectious proteins called prions. As used herein, "seat," "chair," "bench," and "sitting apparatus," have the same meaning and can be used interchangeably. As used herein the back and backrest of a sitting apparatus can have the same meaning and be used interchangeably. In certain embodiments of the invention the seat, chair or bench can be devoid of a filter. It is contemplated that certain aspects of the invention disclosed herein can also be used in beds and other laying apparatus. Indoor or enclosed multi-seated venues as used herein can include vehicles that are land based, sea based and air based (aircraft), theaters and auditoriums. A theater as used herein can include all types of auditoriums. As used herein the word clean can have the same meaning as purify. The words purify and/or clean can imply that of partially cleaned, partially purified, or fully cleaned and fully purified. As used herein an exhaled air purification chamber means the same as an air purification chamber. As used herein an exhaled purification system means the same as an air purification system. An electronic display screen, video display screen, display screen can all have the same meaning. In aspects as used herein, air purification is any mechanism that destroys a pathogen, particulate, and/or a microbe. In aspects as used herein, filtering is a mechanism whereby particulates, pathogens, and/or microbes are captured, segregated, and/or separated.

In further embodiments of the present invention, an air purification chamber may comprise a chamber where exhaled air (including some other cabin air) is cleaned, disinfected, and/or treated. The air purification chamber can use any known mechanism to clean/purify air and filter air, including but not limited to a filter(s), a UVC light(s), a HEPA filter(s), or combinations thereof.

An exhaled air collector may or may not comprise an exhaled catch basin. An exhaled catch basin can be formed in the bottom of an air collector. An air suction intake can be the opening within the exhaled air catch basin that opens to either an attached air purification chamber or to an air suction conduit. When an exhaled catch basin is present, usually, but not always, the air suction intake is located within the exhaled air catch basin. The air suction intake can be the full size of the bottom of the exhaled air catch basin or smaller than the size of the bottom of the exhaled air catch basin. An air collector can open directly to an air suction conduit. In this case the opening to the air suction conduit would be that of the air suction intake.

In certain embodiments of the present invention, an air purification unit captures, cleans, optionally filters, and exhausts cleaned and/or filtered exhaled air directly into the venue where the air purification unit is present. In certain embodiments of the present invention, an air purification unit captures, cleans, optionally filters, and moves cleaned and/or filtered exhaled air out of the venue by way of one or more conduits into the outside environment. In certain embodiments of the present invention, an air purification unit captures, cleans, optionally filters, and moves the cleaned and/or filtered exhaled air by way of one or more conduits into the venue's HVAC system. In certain embodiments of the present invention, an exhaled air collector captures exhaled air where it is then moved to a remote air purification chamber where it is cleaned and/or filtered and then exhausted to an outdoor environment. Such an air purification system is that of an open looped system. In certain embodiments of the present invention disclosed herein, an exhaled air collector captures and moves exhaled air within one or more conduits to a remote air purification chamber where it is cleaned and/or filtered and then moved into the venue's HVAC system where it is then recirculated back into the venue to which it was captured. Such an air purification system is that of a closed looped system. In certain embodiments of the present invention disclosed herein, an exhaled air collector captures and moves exhaled air within one or more conduits into the venue's HVAC system where it is cleaned and/or filtered and then recirculated back into the venue to which it was captured. Such an air purification system is that of a closed looped system. In certain embodiments of the invention, an exhaled air collector connects to an air suction conduit where the non-cleaned and non-filtered exhaled air is moved therethrough and then moved into the venue's air flow that moves the exhaled air out of the venue. In certain embodiments of the invention, an exhaled air collector connects to an air suction conduit where the non-cleaned and non-filtered exhaled air is moved therethrough and then moved into the venue's air flow that moves the exhaled air into the venues HVAC system which then cleans and/or filters the exhaled air. In certain embodiments of the invention, an air collector can capture non-filtered and non-cleaned exhaled air and fan or fans can move the non-filtered, non-cleaned exhaled air along a shaped indentation in the backside of a back of a chair, seat, or bench towards the venue's air flow where the venue's air flow moves the non-filtered, non-cleaned exhaled air out of the venue. In certain embodiments of the invention, an air collector can capture non-filtered and non-cleaned exhaled air and a fan or fans can move the non-filtered, non-cleaned exhaled air along a shaped indentation in the backside of a back of a chair, seat, or bench towards the venue's air flow where the venue's air flow moves the non-filtered, non-cleaned exhaled air out of the venue and into the venue's HVAC system where it can be cleaned and/or filtered. In certain embodiments, the exhaled air collector can be that of combination of a video display screen and its surrounding frame or housing. In this embodiment, the air suction conduit can be an arm that secures or supports the video display screen. The video display screen can be part, or all, of the recessed exhaled air blocking surface.

Certain embodiments of the invention can be that of a chair, seat, or bench that comprises an exhaled air catch basin. Certain embodiments of the invention can be that of a chair, seat, or bench that comprises a conduit for passing non-cleaned and/or non-filtered exhaled air downward towards the floor. Certain embodiments of the invention can be that of a chair, seat, or bench that comprises a shaped indentation on the backside of a back of the chair, seat, or bench for directing non-cleaned and/or non-filtered exhaled air downward towards the floor. Certain embodiments of the invention can be that of a chair, seat, or bench that comprises a fan or fans for moving air downward along the backside of the back of the chair, seat, or bench towards the floor. Certain embodiments of the invention can be that of a chair, seat, or bench that comprises a fan or fans for moving air downward across the recessed exhaled air blocking surface of the exhaled air collector. Certain embodiments of the invention can be that of a chair, seat, or bench that comprises an air collector that is one of attached to, embedded in or within, or integral or shaped within, the backside of a back of the chair, seat, or bench. Certain embodiments of the invention can be that of a chair, seat, or bench that receives an air purification unit. Certain embodiments of the invention can be that of a chair, seat, or bench that is shaped to receive an air purification unit. Certain embodiments of the invention can be that of a chair, seat, or bench that is specially shaped to attach to an air purification unit. Certain embodiments of the invention can be that of a chair, seat, or bench that comprises a video display screen on the back side of a back of the chair, seat, or bench, whereby the video display screen is an exhaled air blocking surface that deflects exhaled air into or towards an air suction conduit.

The following embodiments as disclosed herein include an exhaled air diagnostic, testing component or analyzer device. In aspects, the exhaled air that enters an exhaled air diagnostic, testing component or analyzer device is that of non-cleaned and/or non-filtered exhaled air. Thus, when and if used in conjunction with an exhaled air purification unit or system, the apparatus may comprise and the aspects may be used in the order of: 1) an exhaled air collector, 2) an exhaled air diagnostic, testing component or analyzer device, and 3) an exhaled air purification chamber. In certain embodiments the exhaled air diagnostic, testing component or analyzer device is used solely in conjunction with an exhaled air collector and is devoid of a connected air purification unit or chamber. In certain embodiments of the invention the air purification unit can comprise an exhaled air diagnostic, testing component or analyzer device. In certain embodiments of the invention an air purification unit and/or exhaled air collector can comprise an exhaled air diagnostic, testing component or analyzer device. In certain embodiments of the invention an air purification system can comprise an exhaled air diagnostic, testing component or analyzer device. In certain embodiments of the invention an air purification system can comprise an exhaled air diagnostic, testing component or analyzer device. In certain embodiments of the invention an exhaled air collector on the chair, in the chair, embedded in the chair, integrated within the chair, attached to the backside of the chair, attached to the chair, or free standing, separated, and located directly behind the backside of a chair, can comprise an exhaled air diagnostic, testing component or analyzer device. In certain embodiments of the invention an exhaled air collector can comprise an exhaled air diagnostic, testing component or analyzer device. In certain embodiments of the invention an exhaled air collector on the chair, in the chair, embedded in the chair, integrated within the chair, attached to the backside of the chair, attached to the chair, or free standing, separated, and located directly behind the backside of a chair, can connect to an exhaled air diagnostic, testing component or analyzer device. In certain embodiments of the invention an exhaled air collector on, in, attached to the backside of a chair or free standing, separated, and located directly behind the backside of a chair, can connect to an exhaled air diagnostic, testing component or analyzer device. In certain embodiments of the invention, the exhaled air catch basin can comprise an exhaled air diagnostic, testing component or analyzer device. In certain embodiments of the invention the exhaled air catch basin on the chair, in the chair, embedded in the chair, integrated within the chair, attached to the backside of the chair, attached to the chair, or free standing, separated, and located directly behind the backside of a chair, can comprise an exhaled air diagnostic, testing component or analyzer device. In certain embodiments of the invention an air purification chamber can comprise an exhaled air diagnostic, testing component or analyzer device. In certain embodiments of the invention an exhaled air chamber can comprise an exhaled air diagnostic, testing component or analyzer device. In certain embodiments of the invention an air purification chamber can connect to an exhaled air diagnostic, testing component or analyzer device. In certain embodiments of the invention an air purification chamber can connect to an exhaled air diagnostic, testing component or analyzer device. In certain embodiments of the invention non-filtered and non-cleaned exhaled air can be collected and subjected to an exhaled air diagnostic, testing component or analyzer device that is positioned on, in, or attached to the backside of the back of a chair, seat, or bench. In certain embodiments of the invention non-filtered and non-cleaned exhaled air is collected and tested by an exhaled air diagnostic, testing component or analyzer device that is supported by the backside of the back of a chair, seat, or bench. In certain embodiments of the invention non-filtered and non-cleaned exhaled air is collected by an exhaled air collector that is on, in, attached to or part of the backside of a chair, seat, or bench, or free standing, separated, and located directly behind the backside of a chair, seat, or bench, then transported through a conduit and then tested by an exhaled air diagnostic, testing component or analyzer device that is remote to the backside of a chair, seat, bench. In certain embodiments the exhaled air collector can be that of combination of a video display screen and its surrounding frame or housing. In this embodiment the air suction conduit can be an arm that secures or supports the video display screen. The video display screen can be part of all of the recessed exhaled air blocking surface. The air suction conduit can move the exhaled air to an exhaled air diagnostic, testing component or analyzer device.

In other embodiments of the present invention, specialized seating provides exhaled air collection and diversion. In aspects, a seat is formed, shaped or adapted (in cases, by way of an attachment) to collect and reposition or redirect exhaled air downward through a conduit in the seat or attached to the seat towards an aircraft's floor where it is mixed with the cabin's air handling air flow such that it is moved out of the cabin by the aircraft's air handling air flow. The exhaled air that mixes with the aircraft's air flow can be unfiltered prior to departing the aircraft cabin. This is possible as once it exits the cabin it will either be released outside of the aircraft or filtered, cleaned, and recirculated by the aircrafts air handling and purification system. In aspects, the form, shape, adaptation, or attachment provides a conduit or corridor for air to pass through from the exhaled air collector through the conduit or corridor towards the floor of the aircraft cabin. Seating embodiments that include exhaled air collection and diversion, in aspects, work with an aircraft's existing air handling system, wherein the aircraft's air purification or handling system has air blowing from the ceiling of the aircraft cabin that moves from the ceiling downward towards the floor (usually towards the center aisle) and then under the seats towards the lower inside walls of the aircraft, where air registers/air intakes are located along the cabin of the aircraft. (See FIGS. 8-9.) In aspects, the conduit within or attached to the seat opens above the floor or ground where the exhaled air is mixed with airflow from the aircraft and moved out of the aircraft (or in cases filtered and released back into the aircraft from the overhead vents in the ceiling). In other aspects, the conduit within or attached to the seat moves downward and then the conduit continues either downward or horizontally transporting the exhaled air without being mixed with the air flow in the aircraft cabin and where it opens into the air handling system of the aircraft outside of the aircraft cabin. In FIG. 10, an aspect is shown where exhaled air 1010 from a passenger 1020 is captured by the air purification unit 1030 and a conduit 1040 then leads that air to the bottom of the seat or at or near the floor of the aircraft cabin and then directed to vents 1050 in or near the floor of the aircraft cabin where the exhaled air is removed from the aircraft cabin.

In aspects of the invention, the air purification unit includes the exhaled air collector, an optional exhaled air catch mechanism (e.g., a basin), an air suction conduit, and an air purification chamber. In aspects, there is no fan to direct or suction air and no air curtain. In aspects, the air purification unit may include an air filter but can also be implemented without an air filter. The air purification unit comprises both an air collector and an air purification chamber. UVC light, such as a disinfecting light can be used to destroy pathogens, microbes, or other unwanted materials in the handled air.

In aspects of the invention, the air purification unit includes the exhaled air collector, an optional exhaled air catch mechanism (e.g., a basin), an optional air suction conduit, and a connected air purification chamber. In aspects, a fan may be used to direct or suction air into the air purification chamber and/or a fan, fans, or an air curtain may be used or placed above or on top of the unit to push air downward into, for example, an exhaled air catch basin and/or air suction conduit. In aspects, the unit may include an air filter but can also be implemented without an air filter. The air purification chamber can employ, by way of example only, UVC light, such as a disinfecting light can be used to destroy pathogens, microbes, or other unwanted materials in the handled air.

In aspects of the invention, the air purification unit includes the exhaled air collector, an optional exhaled air catch mechanism (e.g., a basin), an optional air suction conduit, and an air purification chamber. In aspects, a fan is located in a conduit—or connected to, adjacent to, or in operable communication/connection with a conduit—to pull air downward through the conduit towards floor, out of a venue or vehicle, to an air processing system, or elsewhere. In aspects, the unit may include an air filter but can also be implemented without an air filter. The air purification chamber can employ, by way of example only, UVC light, such as a disinfecting light can be used to destroy pathogens, microbes, or other unwanted materials in the handled air.

In aspects of the invention, the air purification unit includes the exhaled air collector, an optional exhaled air catch mechanism (e.g., a basin), an air suction conduit, and the air purification chamber. In aspects, a fan is located in a conduit—or connected to, adjacent to, or in operable communication/connection with a conduit—to pull air downward through the conduit towards a floor, and a fan or air curtain is used to push air downward across, for example, an exhaled air blocking surface, such as a recessed exhaled air blocking surface. In aspects, the unit may include an air filter but can also be implemented without an air filter. The air purification chamber can employ, by way of example only, UVC light, such as a disinfecting light can be used to destroy pathogens, microbes, or other unwanted materials in the handled air.

In aspects, embodiments of the present invention include an exhaled air collector that if built into, attached to a seat back, or separated and located behind a seat back, can block and divert non-filtered exhaled air downward towards the floor of the aircraft cabin when the aircraft's air purification or handling system has air flowing from the ceiling towards the floor and then out of the aircraft (or to another air handling system in the aircraft, such as, by way of example, the aircraft's air purification or handling system or an air purification chamber). (See FIGS. 8-9.) In other aspects, embodiments include an exhaled air collector and an exhaled air blocking surface, such as a recessed exhaled air blocking surface. This embodiment optionally includes a fan or air curtain above or placed on top of the system to push air downward across the recessed exhaled air blocking surface of the exhaled air collector downward towards the optional exhaled air catch basin and then towards the air suction intake.

In other embodiments, the invention comprises an air purification unit releasably attachable to an apparatus, such as the back of a chair. In aspects, the air purification unit includes an exhaled air collector, an optional exhaled air catch basin, an air suction intake, and an air purification chamber. In certain embodiments where the air collector is directly attached to an air purification chamber, there can or will, in aspects, be no air suction conduit present. In most, but not all cases, the air purification chamber exhausts clean air back into the multi-seated indoor or enclosed venue.

In other embodiments, the invention comprises an air purification unit releasably attachable to an apparatus, such as the back of a chair. In aspects, the air purification unit includes an exhaled air collector, an optional exhaled air catch basin, an air suction intake, and an air purification chamber. In embodiments, there would be no air suction conduit as the air purification chamber exhausts clean air back into the multi-seated indoor or enclosed venue. In aspects, a fan within or connected to the air purification chamber may pull air into and out of the air purification chamber.

In other embodiments, the invention comprises an air purification unit releasably attachable to an apparatus, such as the back of a chair. In aspects, the air purification unit includes an exhaled air collector, an optional exhaled air catch basin, an air suction intake, and an air purification chamber. In embodiments, there would be no air suction conduit as the air purification chamber exhausts clean air back into the multi-seated indoor or enclosed venue. In aspects, a fan within or connected to the air purification chamber may pull air into the air purification chamber and a fan or air curtain above may push air across an exhaled air blocking surface, such as a recessed exhaled air blocking surface.

In additional embodiments, an air purification system comprises a plurality of exhaled air collectors, each with an optional exhaled air catch basin, an air suction intake, and an air suction conduit, that connects to one or more remote air purification chambers. In aspects, this unit is a closed loop that takes air from the venue and returns air back into the venue. For example, this system may connect to an HVAC system and then move clean air back into the venue. The HVAC system can clean and/or filter the air (including any non-filtered and or non-cleaned exhaled air) prior to returning it into the venue. In aspects, the system may connect to a humidification regulator or dehumidifier. In other aspects, the system may be open loop, wherein air from the air purification chamber moves air into an outdoor, different, or separate environment.

BRIEF DESCRIPTION OF THE DRAWINGS

The accompanying drawings illustrate certain aspects of some of the embodiments of the present invention and should not be used to limit or define the invention. Together with the written description the drawings serve to explain certain principles of the invention.

FIGS. 25A and 25B are schematics showing aspects of an air purification unit as described herein.

FIG. 26 is a schematic showing aspects of an air purification unit as described herein.

DETAILED DESCRIPTION

Figure 1:
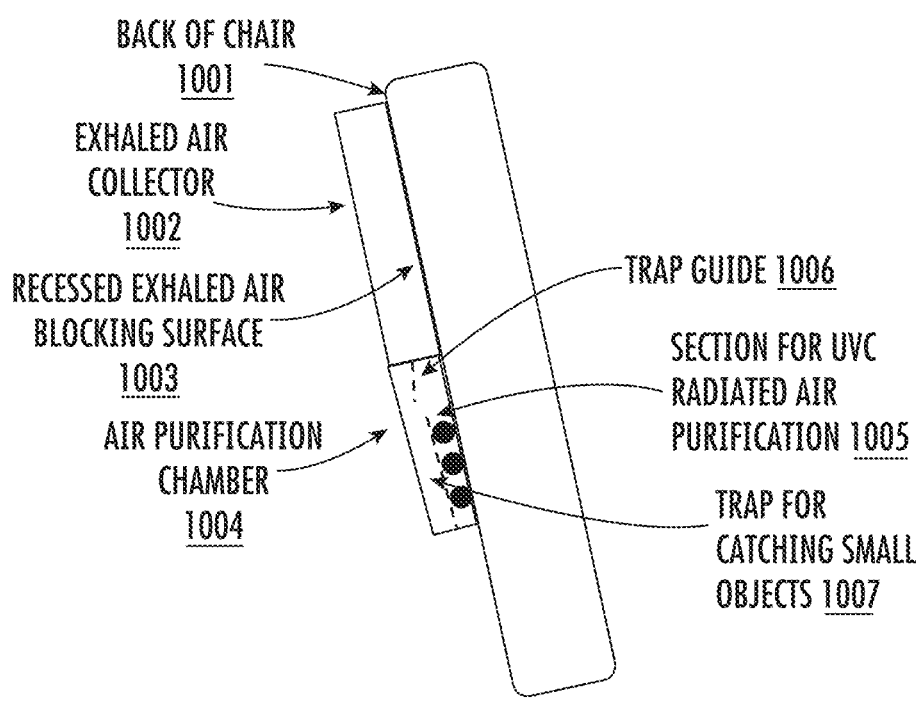
FIG. 1 is a schematic of a possible embodiment according to the present invention showing an air purification unit and back of a chair.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Embodiments comprising various features may also consist of or consist essentially of those various features. Other embodiments of the invention will be apparent to those skilled in the art from consideration of the specification and practice of the invention. The description of the invention provided is merely exemplary in nature and, thus, variations that do not depart from the essence of the invention are intended to be within the scope of the invention.

All references cited in this specification are hereby incorporated by reference in their entireties.

In embodiments, the air purification unit can be one of attached to one or more of the top, side or back of a chair, built into the back of a chair, or behind and free standing/separated from the back of a chair. (See FIGS. 11-13.) In aspects, the air purification unit can be of a size and shape so that when it is attached to the back of a chair some, all, or most of the air purification unit is located within a back overhang space. The air purification unit can be of a size and shape so that when it is attached to the back of a chair the air purification unit can fit within the back overhang space. The air collector of the air purification unit can be located on the back of a chair, seat, or bench and be connected to the air purification chamber that can be located under the seat of the chair, seat, or bench. An air purification unit, in aspects, can be part of an air purification system. An air purification system, in aspects, can comprise a networked plurality of air purification units. An air purification unit, in aspects, may comprise an exhaled air collector and a connected air purification chamber. An air purification unit, in aspects, may comprise an exhaled air collector and be attached to an air purification chamber. An air purification unit, in aspects, may comprise an exhaled air collector and be directly attached to an air purification chamber. An air purification system, in aspects, can comprise a networked plurality of exhaled air collectors that are connected to one or more air purification chambers, such as one or more remote air purification chambers by way of one or more air suction conduits. An air purification system, in aspects, can comprise a plurality of networked air purification units. In certain embodiments, the air purification system can include an HVAC unit. In certain embodiments, the air purification system can include an air humidification unit and/or dehumidifier. In certain embodiments, the air purification system can include both an HVAC system and an air humidification unit and/or dehumidifier. In certain embodiments, the air purification system can include an air blower or air curtain that provides downward air flow from above the air collector. In embodiments, the exhaled air collector can be adjacent to and/or connected to an air purification chamber. The exhaled air collector can comprise an exhaled air blocking surface. An exhaled air blocking surface can be an exhaled air deflecting surface. The exhaled air blocking surface in certain embodiments can be recessed and comprise two or more walls. In embodiments, the exhaled air collector can comprise a recessed exhaled air blocking surface that has two walls that connect to a lower exhaled air catch basin. The walls of the exhaled air collector can be comprised of a flexible material, by way of example only, rubber, plastic, or a material that is comprised by a chair, seat, bench (e.g., the same material that the chair, seat, or bench to which the exhaled air collector is associated with is made of). The walls of the exhaled air collector can be rigid. The exhaled air blocking surface can be, by way of example only, one or more of a metal, plastic, glass, ceramic, or rubber surface. The exhaled air blocking surface can be that of an electronic video display. An exhaled air catch basin can be located within and/or connected to a bottom ⅓ of the exhaled air blocking surface. The exhaled air catch basin can be located at the bottom of the exhaled air blocking surface. In certain embodiments, the exhaled air collector connects to a conduit and is devoid of an exhaled air catch basin. In certain embodiments the exhaled air collector connects to a conduit and may include an exhaled air catch basin or not include an exhaled air catch basin. In other embodiments, the exhaled air collector connects to an exhaled air catch basin. In aspects, an air suction intake can be connected to an exhaled air collector. In aspects, an air suction intake can be connected to an exhaled air catch basin. The exhaled air catch basin can comprise an air suction intake that is an opening that opens directly to an air purification chamber or an air suction conduit.

In certain embodiments, an air purification unit can be modular and can be releasably attached and thus removable from the back of a seat, chair, or bench, or from a free-standing stand that supports an air purification unit that is separate, and distance removed from the back of a seat, chair, or bench. The air purification unit can be designed so that if a small object falls through an air suction intake it will not fall into the air purification chamber. This can be accomplished, by way of example only, by a safety trap that catches such a small object within the trap but allows the exhaled air to continue to be moved through an air purification chamber or elsewhere. A screen or grate covering can be placed over the exhaled air catch basin. A screen or grate covering can be placed over the exhaled air collector. A screen or grate covering can be placed over an air suction intake. In aspects, the screen or grate can comprise one or more of Copper (Cu+), Copper (Cu++), Silver, Zinc, Gold, TiO2, metal, or plastic. (See, e.g., FIG. 3.)

In certain embodiments an air purification unit can be filter-less (without a filter). In certain embodiments, filter-less air purification units can be attached to one or more of the top, side, or back of a chair, built into the back of a chair, or be behind, free standing, and separated from the back of a chair in a multi-seated indoor or enclosed venue (such as, by way of example only, theaters of all kinds and vehicles of all kinds). In certain embodiments the air purification system or a plurality of air purification units can work in conjunction or coordination with the HVAC system, air purification, or air handling system of the multi-seated indoor venue. In this case the venue's HVAC system, air purification, and/or air handling system is independent from that of a plurality of air purification units and/or the air purification system described herein. In this embodiment, for example, the filter-less air purification units may be utilized to destroy airborne pathogens especially from exhaled air, while the venue's HVAC, air purification system, or air handling system can be utilized to remove pollutants and any remaining pathogens. By utilizing filter-less air purification units, maintenance time and cost related to changing out filters can be reduced. In addition, this can provide for a quieter indoor venue by way of reducing the noise produced by a plurality of air purification units that comprise filters. In still other embodiments, the air purification unit(s) can comprise a filter (and/or UVC lights) that is used in combination with the indoor or enclosed venue's HVAC system or air handling system.

In certain embodiments an exhaled air collector can collect non-cleaned, non-filtered exhaled air, and an air suction intake can then move the non-cleaned, non-filtered exhaled air through an air suction conduit that is attached to, supported by, or located within the back of a chair, seat, or bench, and then release the non-cleaned, non-filtered exhaled air within the multi-seated indoor venue. In this embodiment, the venue's HVAC system can clean and/or filter the non-cleaned and/or non-filtered exhaled air.

In certain embodiments, the air collector can comprise a filter or HEPA filter. In certain embodiments, the air purification chamber can comprise a filter or HEPA filter. In other embodiments, the air collector and/or the air purification chamber can be devoid of a filter or HEPA filter. The air purification chamber can comprise one or more of, by way of example only, a microbicidal and/or disinfecting light, material, agent, or element. With the various embodiments, one or more of the exhaled air collector, the exhaled air blocking surface, the air catch basin, the air suction conduit, or a grate or screen that is used as a cover, can comprise a microbicidal agent, element, or material.

In many cases of human breathing, following an exhaled breath of air there is a 3 to 5 second pause of the exhaled air stream while the individual who was exhaling air now inhales air. Said another way, after each exhaled air breath in most cases there is a 3 to 5 second pause in the exhaled air stream. In aspects of the current invention, this exhaled air stream pause, along with gravity, and in some cases downward air flow, assists in moving the exhaled air into the exhaled air collector and/or the optional air catch basin and through the air suction intake. The exhaled air collection section and the air purification chamber has the capability/capacity to collect, clean, optionally filter, and/or purify, in cases, a minimum of 0.21188 cubic feet per minute of air. The air collection section (the exhaled air collector) can collect a minimum of 0.2 liters of exhaled air within a 6 second interval of time. The air purification chamber, in cases, can clean a minimum of 0.2 liters of air within a 6 second interval of time. In most cases, the exhaled air collector can collect 20 liters or more of exhaled air per minute. In most cases, the exhaled air purification chamber can clean 20 liters or more of exhaled air per minute. A fan or fans may be used to move air into and/or through air purification unit, and such fan or fans can operate at 5 CFM or greater. A fan or fans used to move air into and/or through an air suction intake can operate at 5 CFM or greater. A fan or fans used to move air through an air suction conduit or conduits to a remote air purification chamber can operate at 100 CFM or greater.

The invention disclosed herein may be applied to or used in any and all kinds of multi-seated venues or environments, such as, by way of example only, land based, sea based, or air based vehicles (such as, by way of example only, aircraft, airplanes, jets, boats, ships, cars, automobiles, trucks, trains, subways, buses, etc.), theaters (such as, by way of example only, auditorium, educational, sports, athletic, performing arts, cinema, opera, ballet, music, arena, etc.), houses of worship (such as, by way of example only, churches, synagogues, temples, mosques, etc.). Inventions disclosed herein can include, in various embodiments, each of an attachable, integrated, or independent air purification system, air purification unit, exhaled air collector, and/or air purification chamber, as well as, in aspects, a chair, seat, bench, or sitting or laying apparatus wherein the chair, seat, bench, or sitting or laying apparatus is adapted or designed to house, support, integrate, attach, connect, or incorporate such an air purification system, air purification unit, exhaled air collector, and/or air purification chamber. Also, in certain embodiments, the back of a chair, seat, bench, or a sitting or laying apparatus, can be designed so that the shape of the back of the chair, seat, bench, or the sitting or laying apparatus, or parts thereof, can be formed into that of an exhaled air collector. In aspects, this is accomplished by way of the shape of the back side of the back of the chair. By way of example only, in one particular embodiment, the back of the chair can be designed so that the shape of the back side of the back of the chair can be that of an exhaled air collector, such that it comprises a recessed blocking surface surrounded by one, two, or more walls that open and connect to where an air purification chamber can then be inserted into the back of the chair. In another embodiment, the back side of the back of the chair can be designed so that it has a recessed blocking surface surrounded by one, two, or more walls that open to an exhaled air catch basin which is also part of the shape design of the back of the chair. An air purification chamber can be inserted or attached to the back of the chair such that the exhaled air catch basin opens to the separate air purification chamber. In still another embodiment, the back side of the back of a chair can be designed so that the shape of the back side of the back of the chair can be that of an exhaled air collector having a recessed blocking surface surrounded by one, two, or more walls that open or attach to an air conduit located within the chair or attached to the chair that then connects to a remote air purification chamber. Thus, an embodiment disclosed herein can be that of a novel shaped chair, seat, bench, or sitting or lying apparatus, or parts thereof, that act as the exhaled air collector for the air purification unit or that of the exhaled air collector for the air purification system. In certain embodiments, the back of the chair, seat, or bench can comprise the appropriate shape and include electronic and non-electronic components (as taught herein) that permit the chair, seat, or bench to include an air purification unit. By this it is meant that the chair, seat, or bench is designed and equipped such that the chair, seat, or bench itself becomes both an exhaled air collector and the air purification chamber. Such a chair, seat, or bench may or may not employ/comprise an air filter.

The use of the term conduit as used herein is, in aspects, that of a corridor, tube, hose, channel, tunnel, or other mechanism for moving, directing, or allowing air to move or pass, such as from one location to another. The conduit can be located within the back of a seat, chair, bench, or sitting apparatus, or attached/connected to the back of a seat, chair, bench, or sitting apparatus. The conduit can be a conduit that runs from a seat, chair, bench, or sitting apparatus to a remote air purification chamber. The conduit can be made of any material that provides for a corridor capable of isolating and allowing air to pass through.

In still another embodiment of a chair/seat for an aircraft, the back of the seat/chair can be formed/shaped to be that of an exhaled air collector having an opening such that exhaled air is captured by the exhaled air collector and then moved downward through a conduit within the chair/seat or attached to the chair/seat to the floor of the aircraft cabin where it can be moved out of the cabin of the aircraft by way of the air flow circulation of the aircraft. In most, but not all, cases, this exhaled air is non-cleaned and/or non-filtered exhaled air. In this embodiment, the aircraft's air purification and/or handling system takes over once the exhaled air is captured by the aircraft's air handling system's air flow near the floor of the aircraft. The aircraft's air flow then moves the non-cleaned and/or non-filtered exhaled air out of the cabin of the aircraft, where the aircraft's air handling system and/or purification system causes part or all of the non-cleaned and/or non-filtered exhaled air to exit the aircraft, or in certain cases cleans and/or filters all or some of this non-cleaned and/or non-filtered exhaled air and then recirculates the now cleaned and/or filtered exhaled air back into the aircraft cabin. (See, e.g., FIGS. 8-9.) In this embodiment, part or all of the recessed exhaled air blocking or collection surface can be that of a video display screen. (See, e.g., FIGS. 15-16, 21-24, and 26.) In other embodiments, the video display screen is positioned in front of the recessed exhaled air blocking or collection surface. As taught herein an exhaled air collector can comprise a fan or fans that move air downward across the recessed exhaled air blocking or collection surface. (See FIG. 7A.) In certain cases, a fan or fans can be incorporated within or attached to the exhaled air collector and in other cases no fan is utilized. In still other cases, a fan or fans can be located within an air conduit located within or attached to the chair/seat. In aspects, the conduit connects on one end to the exhaled air collector and on the other end opens to expel the exhaled air under or beside the chair/seat. (See, e.g., FIGS. 9-10 and 14.) In this embodiment the aircraft's air purification or handling system's air flow then moves the exhaled air out of the aircraft cabin, where it is moved out of the aircraft or is cleaned and/or filtered and recirculated back into the aircraft cabin. (See, e.g., FIGS. 8-10.)

In still another embodiment of a chair/seat for an aircraft, the back of the seat/chair can be formed/shaped to be that of an exhaled air collector having an opening such that exhaled air is captured by the exhaled air collector and then moved downward through an air suction conduit within or attached to the chair/seat to the floor where, in aspects, it can be moved out of the cabin by way of an air suction conduit (and/or a fan or fans located within the air suction conduit, and/or the aircraft's air purification or handling system). The air suction conduit can open adjacent to that of the aircraft's air flow register or air intake or within the aircraft's air flow register or air intake, which, in aspects, is located near or within a wall or floor of the cabin. The air suction conduit can open into the aircraft's air handling or air purification system. With this embodiment, in aspects, the recessed exhaled air blocking surface can be part, or all of, that of a video display screen. (See, e.g., FIGS. 15-16, 21-24, and 26.) In other embodiments, the video display screen can be in front of the recessed exhaled air blocking surface. As taught herein, an exhaled air collector can comprise a fan or fans that move air downward across the recessed exhaled air blocking surface. In certain cases, a fan or fans can be incorporated within or attached to the exhaled air collector and in other cases no fan is utilized. In still other cases, a fan or fans can be located within or attached to an air conduit located within or attached to the chair/seat. In aspects, the conduit connects on one end to the exhaled air collector and on the other end connects to an air suction conduit, which moves the exhaled air to an air purification chamber, such as a remote air purification chamber. (See, e.g., FIG. 18.)

In another embodiment of a chair/seat for an aircraft, an exhaled air collector can be attached to or integrated within the chair/seat back comprising an opening such that exhaled air is captured by the exhaled air collector and then moved downward through an air suction conduit within the chair/ seat or attached to the chair/seat towards the floor where it exits the air suction conduit and can be moved out of the cabin of the aircraft by way of the air flow circulation of the aircraft. In this embodiment the aircraft's air purification or handling system takes over once the exhaled air is captured by the aircraft's air purification or handling system's air flow near the floor of the aircraft cabin. For this reason, the air collector, seat/chair, and conduit are filter-less, in aspects. With this embodiment, part or all of the recessed exhaled air blocking surface can be that of a video display screen. As taught herein, an exhaled air collector can comprise a fan or fans that moves air downward across the recessed exhaled air blocking surface. In certain cases, a fan or fans can be incorporated within or attached to the exhaled air collector and in other cases no fan is utilized. In still other cases, a fan or fans can be located within or attached to an air conduit that can be attached to the seat or located within the seat. In aspects, the conduit connects on one end to the exhaled air collector and on the other end opens to expel the exhaled air under the chair/seat. In this embodiment, the aircraft's air purification or handling system's air flow then moves the exhaled air out of the aircraft cabin where all or part of it is removed from the aircraft and the balance is cleaned and/or filtered by the aircraft's air purification system and then recirculated back into the aircraft's cabin.

Another embodiment of the present invention is that of a chair, seat, bench, or sitting apparatus wherein the backside of the chair, seat, bench, or sitting apparatus comprises an indentation capable of capturing or redirecting exhaled air that, in aspects, begins within the top ⅓ of the back side of the chair, seat, bench, or sitting apparatus and extends to a point opposite or farther down than that of an extended horizontal tray that is attached to the back of the chair, seat, bench, or sitting apparatus, and wherein exhaled air can be directed or moved downward towards the floor where it is moved out of the passenger compartment of the vehicle by way of the vehicle's air flow.

In another embodiment of a chair/seat for an aircraft, an exhaled air collector can be attached to or integrated within the chair/seat back and comprises an opening such that exhaled air is captured and/or deflected by the exhaled air collector and then moved downward through a conduit within the chair/seat or attached to the chair/seat to the floor where it can be moved out of the cabin by way of an air suction conduit that moves the exhaled air to a remote air purification chamber. In this embodiment, part, or all, of the recessed exhaled air blocking surface can be that of a video display screen. As taught herein an exhaled air collector can comprise a fan or fans that moves air downward across the recessed exhaled air blocking surface towards an air suction intake. In certain cases, a fan or fans can be incorporated within or attached to an exhaled air collector and in other cases no fan is utilized. In still other cases, a fan or fans can be located within or attached an air suction conduit that can be attached to the seat/chair, located within the seat/chair, or comprise part of the seat/chair. The air suction conduit can connect on one end to the exhaled air collector. The other end of the air suction conduit can connect to that of a remote air purification chamber. The air suction can be provided by a fan or fans located within one or more of the air suction conduits, the remote air purification system, or a remote air handling system.

In still another embodiment of a chair/seat for a vehicle, the back of the seat/chair can be formed/shaped to be that of an exhaled air collector having an opening such that exhaled air is captured and or deflected by the exhaled air collector and then moved downward through a conduit within the chair/seat or attached to the chair/seat to the floor where it is then moved out of the vehicle and exhausted into a different environment, such as an outside environment, and/or it is cleaned and/or filtered by a remote air purification chamber located within the vehicle. A fan or multiple fans can be utilized to assist in moving the exhaled from the exhaled air collector to the different environment, such as the outside environment. In another embodiment of a chair/seat for a vehicle, an exhaled air collector can be attached to or integrated within the chair/seat back having an opening such that exhaled air is captured by the exhaled air collector and then moved downward through a conduit within the chair/seat or attached to the chair/seat to the floor where it is then moved out of the vehicle and then exhausted into a different environment, such as the outside environment. A fan or multiple fans can be utilized to assist in moving the exhaled from the exhaled air collector to the different environment, such as the outside environment, or it is moved into a remote air purification chamber located within the vehicle.

In still another embodiment of a chair/seat for a vehicle, the back of the seat/chair can be formed/shaped to be that of an exhaled air collector having an opening such that exhaled air after being captured and/or deflected by the exhaled air collector is then moved downward through a conduit within the chair/seat or attached to the chair/seat and then moved through a conduit to a remote air purification chamber. A fan or multiple fans can be utilized to assist in moving the exhaled from the exhaled air collector to the remote air purification chamber. In aspects, a chair, seat, bench, or sitting apparatus, can be designed to redirect and/or capture exhaled air from someone sitting behind the chair, seat, bench, or sitting apparatus, and wherein the back of the chair, seat, bench, or sitting apparatus is shaped to form or accept an exhaled air collector. The chair, seat, bench, or sitting apparatus can comprise a conduit or can be attached to a conduit for moving the captured exhaled air collected by the exhaled air collector downward towards the floor. The conduit in embodiments described herein can be a tunnel-like opening formed within the seat/chair or can be a separate piece of conduit, by way of example only, one of a plastic, rubber, or metal conduit.

In another embodiment, the chair/seat is shaped/designed such that the back side of the back of the seat acts to deflect exhaled air from someone sitting behind the back of the seat downward towards the floor. In certain cases, the deflected exhaled air is captured by an exhaled air collector. In certain cases, the deflected exhaled air is captured by an exhaled air catch basin. In certain cases, the deflected exhaled air moves through an internal conduit formed within the chair/seat. In certain cases, the deflected exhaled air moves through a conduit attached to the chair/seat. And in certain cases, the deflected exhaled air is directed and moves downward towards the floor along a shaped indentation within the backside of the back of a chair/seat.

In embodiments, an invention disclosed herein is that of a personal air purification unit, wherein the personal air purification unit is one of attachable to the back of a first seat or chair, integrated into the back of a first seat or chair, or free standing behind the back of a first seat or chair, wherein the air purification unit comprises a surface that blocks exhaled air of an individual sitting in a seat or chair behind the first seat or chair, wherein the exhaled air blocking surface is recessed from a peripheral external surface area of the back of the first seat or chair or that of the air purification unit, and wherein exhaled air moves through an air intake to a chamber that purifies the exhaled air. The recessed air blocking surface can be located within an exhaled air collector.

An air intake can be an air suction intake. The air suction intake can be connected to an air suction conduit which then moves the exhaled air to an air purification chamber. The air suction intake can be the opening to an air suction conduit or an attached or connected air purification chamber. In certain embodiments, the air purification chamber can be connected but remote from the exhaled air collector. In other embodiments, the air purification chamber can be integrated within or attached to the exhaled air collector. The air purification chamber, in aspects, can utilize any or all of microbicidal energy, agents, materials, devices or components, including by way of example only, UVC light or Far UVC light. The air purification chamber can utilize microbicidal light, liquids, agents, or materials. The air purification chamber can comprise a filter, such as a HEPA filter. The air purification unit and/or the air purification chamber can be filter-less.

The exhaled air collector can comprise a HEPA filter. The air purification chamber can utilize heat, such as an amount of heat sufficient to be microbicidal. The exhaled air blocking surface of the exhaled air collector can be recessed. In aspects, the recessed exhaled air blocking surface of the exhaled air collector can be recessed between 0.25 inches and 6 inches from that of an external peripheral area of the air purification unit or the back of a chair or seat to which it is attached to, integrated within, or separated therefrom. For example, the recessed exhaled air blocking surface of the exhaled air collector can be recessed between 0.25 inches and 6 inches into a backside of the back of a chair or seat. The recessed exhaled air blocking surface can be recessed between 0.25 inches and 12 inches from the wall heights of the exhaled air collector. In certain embodiments, the location or position of the air purification unit can be adjustable vertically up or down. In certain embodiments, the location or position of the exhaled air collector can be adjustable vertically up and/or down. The vertical dimension of the exhaled air collector can be long enough to capture exhaled air from either an average sized adult and/or an average sized child. In embodiments where the exhaled air collector is not positioned properly to allow for capturing exhaled air from either that of an average sized child or adult, the exhaled air collector can be attached to vertical tracks that allow it to move up and/or down vertically.

The exhaled air collector can be positioned on, in, or separated from the back of the seat or chair such that it is capable of capturing 50% or more of exhaled air of an adult or child of average height and weight sitting directly behind the seat or chair incorporating the air purification unit and/or to which the air purification unit is located. The air purification unit can be designed to accommodate a minimum volume of an adult's exhaled air per minute which is, in cases, around 6 liters per minute. The air purification chamber can have the capability to clean and/or purify a minimum of 0.21188 cubic feet per minute, which equates to the speed and quantity of an average adult's exhaled air. Thus, in aspects, the air purification unit can clean and/or purify up to 100% of the exhaled air of an individual sitting in the seat directly behind that of the back of the seat or chair comprising or having the air purification unit.

The exhaled air collector can comprise an exhaled air blocking surface. The exhaled air blocking surface can be recessed from the periphery of the exhaled air collector or the chair or seat to which it is attached or integrated. The exhaled air blocking surface can be within 45 degrees of being perpendicular to the Z axis from an individual sitting directly behind the seat or chair to which the air purification unit is attached, integrated, or separated and free standing. Exhaled air from an individual sitting directly behind the seat or chair to which the air purification unit is attached, integrated, or separated and free standing, can strike the exhaled air blocking surface within 45 degrees of an angle being perpendicular to said exhaled air blocking surface. The exhaled air collector can comprise a fan or fans located within the upper 33% of the air purification unit. This upper fan or fans can push air downward across and/or parallel to the recessed exhaled air blocking surface. In aspects, the air purification unit can utilize 2 fans: one for pushing air downward from above the recessed exhaled air blocking surface and one for moving air downward below the recessed exhaled air blocking surface. The air purification unit can comprise one fan. The air purification unit can comprise no fan. The air suction conduit can comprise one or more fans. The air suction conduit can comprise no fans.

The downward air flow from an upper fan can help move exhaled air downward towards the air suction intake. In certain situations, an upper fan can pull or direct exhaled air that may go over the top of the exhaled air collector downward so to move it towards the lower air suction intake. In certain embodiments, a lower fan is located within the air suction intake. In other embodiments, the lower fan is located above the air suction intake. In still other embodiments, the lower fan is located within an air conduit. In still other embodiments, the lower fan is located within the air purification chamber. The upper fan can, in aspects, move air downward across or parallel to the recessed exhaled air blocking surface. The lower fan can, in aspects, move air towards or through the air suction intake. In certain embodiments, a fan is utilized to move exhaled air towards the air suction intake. In other embodiments such a fan is not required. The air purification unit can be powered by battery power (DC) or alternating current (AC). If battery powered, it can be a rechargeable battery.

Other air purification unit embodiments can be devoid of a fan and rely on gravity and/or the trajectory of the exhaled air. In certain embodiments, the air collector is devoid of a fan. However, in such a case, a fan may be located within or attached to the connected air purification unit, the air purification chamber, the air suction intake, or the air suction conduit, which creates air suction. This air suction moves the exhaled air from the exhaled air collector through the air suction intake and into the air purification chamber. The air purification unit, or the seat, chair, or bench to which the air purification unit is attached or integrated, can support a video display screen. The air purification unit, or the seat, chair, or bench to which the air purification unit is attached or integrated, can support audio speakers. The video display can be located within the recessed area of the exhaled air collector. The front of the video display can be part, or all, of the recessed exhaled air blocking surface located within the exhaled air collector. Downward air flow from above the air purification unit or the chair or seat can work to enhance the quantity of exhaled air captured by the exhaled air collector. This is true, by way of example only, in a theater multi-seated indoor venue where the floor is sloped and/or within a vehicle.

The exhaled air collector can comprise a recessed exhaled air blocking surface and exhaled air catch basin. All or a portion of the air suction intake can be located below the exhaled air blocking surface in such a manner where the exhaled air is first deflected off of the exhaled air blocking surface and moved towards the air suction intake. All or a portion of the air suction intake can be located within a lower portion of the exhaled air blocking surface. The recessed exhaled air blocking surface can have a horizontal dimension for a theater seat that is greater than 6 inches. The recessed exhaled air blocking surface can have a horizontal dimension for a vehicle seat that is greater than 6 inches. The recessed exhaled blocking surface can be surrounded on two or more sides by walls. The vertical dimension of the recessed area can be greater than 6 inches for both a theater seat and a vehicle seat. The recessed depth can be 0.25 inches or greater for a theater seat and/or a vehicle seat. The recessed depth can be 1 inch or greater for a theater seat and/or a vehicle seat. The recessed depth can range between 0.25 inches and 12 inches, in aspects. The recessed exhaled air blocking surface can form at its bottom an exhaled air catch basin to which exhaled air flows into prior to being removed by the air suction intake. The air suction intake can be located within the bottom of the air catch basin. The exhaled air catch basin can be part of the exhaled air collector. The exhaled air catch basin can be an extension of the exhaled air collector.

The exhaled air catch basin can be attached to the exhaled air collector. The exhaled air blocking surface can be located within 45 degrees of being perpendicular to the floor or ground. The exhaled air catch basin can have an air suction intake within the recessed air blocking surface. The exhaled air catch basin can have an air suction intake within the lower wall of the air catch basin. The exhaled air catch basin can have an air suction intake within the bottom of the air catch basin. The exhaled air catch basin can have an air suction intake within an outer wall of the catch basin. The exhaled air catch basin can be covered with a grate or screen covering. The grate or screen covering can comprise one or more of Copper (Cu+), Copper (Cu++), Silver, Zinc, Gold, $TiO_2$, metal, or plastic. The exhaled air catch basin can be uncovered. The exhaled air catch basin can have a lip-like wall on its front side. With the addition of the lip-like wall on its front side, the exhaled air catch basin can have four vertical walls, a bottom, and an open top. (See, e.g., FIG. 4.)

The air purification unit can comprise a sensor capable of determining if someone is sitting directly behind the seat to which the air purification unit is attached or integrated. The sensor can be, by way of example only, an infra-red sensor, thermal sensor, or motion detector. In aspects, the air purification unit can turn on automatically when someone is sitting directly behind the seat to which the air purification unit is attached or integrated. In aspects, the air purification unit can turn off automatically when someone sitting directly behind the seat to which the air purification unit is attached or integrated leaves their seat. The air purification unit's inner and/or outer surface can be made of a microbicidal material. The air purification unit's inner and/or outer surface can comprise a microbicidal agent. The air purification chamber can comprise a surface that is microbicidal. The air purification chamber's inner surface can be reflective. The reflective material can be, by way of example only, a reflective PTFE plastic material, a reflective polytetrafluoroethylene material, or a reflective Teflon plastic material. The air purification chamber can comprise a fan or fans. The air purification chamber can comprise an ozone detector and an ozone alter mechanism.

A fan comprising part of the air purification unit can be attached to an acoustic reducing material. The air purification unit can comprise an acoustic reducing material. The conduit can be comprised of an acoustic reducing material. The air purification unit can attach to the top of a back of a seat or chair or to the top of the back of the seat or chair. The air purification unit can attach to a side or sides of a seat or chair. The air purification unit can attach to the back of a seat or chair. The air purification unit can be integrated into the back of a seat or chair and a recessed surface of the air purification unit can be located within the back of a seat or chair. The air purification unit can be integrated into the back of a seat or chair and a recessed surface of the air purification unit can be positioned within an indentation of back side of the back of a seat or chair.

The air purification unit can comprise a fan located at the top of the recessed exhaled air blocking surface or located above the recessed exhaled air blocking surface. The air purification unit can comprise a fan located at the bottom of the recessed exhaled air blocking surface or below the recessed exhaled air blocking surface. The air purification unit can be devoid of a fan. An air purification chamber that is adjacent to the air purification unit can comprise a fan at its top and/or at its bottom. The exhaled air collector can comprise a fan located at the top of the recessed exhaled air blocking surface or located above the recessed exhaled air blocking surface. The exhaled air collector can comprise a fan located at the bottom of the recessed exhaled air blocking surface or located below the recessed exhaled air blocking surface. The exhaled air collector can be devoid of a fan. An air purification chamber that is adjacent to the exhaled air collector can comprise a fan at its top. An air purification chamber that is adjacent to the exhaled air collector can comprise a fan at its bottom. An air purification chamber that is integrated into the air purification unit can comprise a fan at its top. An air purification chamber that is integrated into the air purification unit can comprise a fan at its bottom. The air purification unit can work in conjunction with overhead downward air flow. The air purification unit can work without downward air flow.

The air purification unit can be located above knee height of an individual sitting directly behind the seat to which the air purification unit is attached or integrated. In cases, the air purification unit means, by way of example only, the following aspects: the exhaled air collector, an optional exhaled air catch basin, the air suction intake, an optional air suction conduit, and the air purification chamber. The air purification system can also optionally include one or more of: an HVAC system, a dehumidifier, a humidifier, and/or an air curtain or fan(s) for pushing disinfected, cleaned, filtered, or unfiltered air back into the venue. The air curtain or fan(s) can be located above the seating in the multi-seated venue. The air curtain or fan(s) can be positioned such to move exhaled air towards an exhaled air collector. In certain embodiments, a networked air purification system utilizes an open loop wherein disinfected, cleaned, filtered, or unfiltered air is provided into the multi-seated venue before being moved to an HVAC (or air handling) system or outside of the multi-seated venue. In aspects, when the air purification system comprises a dehumidifier, the level of humidity is maintained within the multi-seated venue at 30% to 60% relative humidity. The air sterilization system can utilize a dehumidifier to achieve and maintain the desired range of relative humidity within the indoor venue.

In aspects, the air purification system comprises a plurality of exhaled air collectors that connect to one or more remote air purification chambers. In other embodiments, the networked air purification system operates as a closed looped system wherein the disinfected, cleaned, filtered, or unfiltered air is moved into one or more of the venue's HVAC system, an air purification system, or an air handling system, and then back into the multi-seated venue. In an embodiment of the air purification system, multiple exhaled air collectors are connected by way of air suction conduits, for example, to one or more remote air purification chambers, which can then move disinfected, cleaned, filtered, or unfiltered air back into the venue or to the venue's HVAC or air handling system, or to a different environment, such as an outside environment.

In embodiments wherein the exhaled air purification system comprises a plurality of exhaled air collectors that connect to one or more remote air purification chambers, the one or more remote exhaled air purification chambers can connect to an HVAC or air handling system. In still other embodiments, two or more exhaled air collectors can connect to a remote exhaled air purification chamber or more than one air purification chamber.

An exhaled air purification unit can be attached to, integrated into, or free standing and separated from the back of a seat or chair. The exhaled air purification chamber can utilize UV light. UV light used in an exhaled air purification chamber can be that within the range of 100 to 400 nanometers. In most cases the UV light is that of UVC light having a wavelength within the range of 100 to 280 nanometers. The UV light can also include far UVC light having a wavelength of or around 222 nanometers+/−3 nanometers. Such an exhaled air purification chamber can be part of an exhaled air purification unit, or can be part of an exhaled air purification system.

The air purification unit can be comprised of a microbicidal material, such as, by way of example only, copper, silver, zinc, copper ions, silver ions, silver nanoparticles, TiO2 nanoparticles, ZnO nanoparticles, organic compounds, and/or hybrids of organic/inorganic nanoparticles. The exhaled air collector can be comprised of a microbicidal material, such as, by way of example only, copper, silver, zinc, copper ions, silver ions, silver nanoparticles, TiO2 nanoparticles, ZnO nanoparticles, organic compounds, and/or hybrids of organic/inorganic nanoparticles. The air purification unit can be covered with a microbicidal material, such as, by way of example only, copper, silver, zinc, copper ions, silver ions, silver nanoparticles, TiO2 nanoparticles, ZnO nanoparticles, organic compounds, and/or hybrids of organic/inorganic nanoparticles. The exhaled air blocking surface and/or the air catch basin can comprise a microbicidal material, such as, by way of example only, copper, silver, zinc, copper ions, silver ions, silver nanoparticles, TiO2 nanoparticles, ZnO nanoparticles, organic compounds, and/or hybrids of organic/inorganic nanoparticles. The air suction intake can be comprised of a microbicidal material, such as, by way of example only, copper, silver, zinc, copper ions, silver ions, silver nanoparticles, TiO2 nanoparticles, ZnO nanoparticles, organic compounds, and/or hybrids of organic/inorganic nanoparticles. The air purification chamber can be comprised of a microbicidal material, such as, by way of example only, copper, silver, zinc, copper ions, silver ions, silver nanoparticles, TiO2 nanoparticles, ZnO nanoparticles, organic compounds, and/or hybrids of organic/inorganic nanoparticles. The interior of the air purification unit or an air purification chamber can comprise an electrostatic surface, such to attract pathogens to its surface.

The air purification chamber can comprise one or more of the following: a filter, a HEPA filter, UVC light, Far UVC light, germicidal light, plasma, heat, or microbicidal materials, such as, by way of example only, copper, silver, zinc, copper ions, silver ions, silver nanoparticles, TiO2 nanoparticles, ZnO nanoparticles, organic compounds, hybrids of organic/inorganic nanoparticles, alcohol, hydrogen peroxide, and/or iodine. The air suction intake can be comprised of a microbicidal material, such as, by way of example only, copper, silver, zinc, copper ions, silver ions, silver nanoparticles, TiO2 nanoparticles, ZnO nanoparticles, organic compounds, and/or hybrids of organic/inorganic nanoparticles. The air suction intake can have a cover and the cover can be comprised of a microbicidal material, such as, by way of example only, copper, silver, zinc, copper ions, silver ions, silver nanoparticles, TiO2 nanoparticles, ZnO nanoparticles, organic compounds, and/or hybrids of organic/inorganic nanoparticles.

In aspects, UV and/or germicidal bulbs used within the air purification chamber should provide appropriate radiation to inactivate or destroy pathogens or a targeted pathogen. The level of radiation required is, in aspects, dependent upon the time in which the pathogen is exposed while moving through the air purification chamber. The air purification chamber and/or air purification unit can comprise a UV sensor or sensors capable of measuring a level of UV radiation. The UV sensor or sensors can monitor the level of UV radiation within the air purification chamber and provide an alert or information via, by way of example only, a light, flashing light, alarm, noise, visual cue, or sending an electronic message should the level of UV radiation of a UV bulb fall below that of a preset threshold, by way of example only, below 50% of the manufacturer's specification of the UV radiation level.

In aspects, each air purification unit can utilize sensor-based self-diagnostics, as well as communicate either wired or wirelessly to a remote computer, such as a laptop, desktop, cell phone, iPad, etc. that can identify if/when certain parts, such as, by way of example only, a filter, fan, light, battery, or sensor, need to be replaced, or if ozone is found above a preset threshold. In embodiments, the air purification unit can be removable (and replaceable) from a chair or seat to which it is attached or integrated. In embodiments, the air purification unit can also be removable and attachable (and replaceable) when it separately is located behind the seat/chair. In embodiments, the air purification unit can be releasably attachable to a chair or seat, such that it can be attached to a chair or seat and removed from a chair or seat. The video display screen that can be attached to or integrated within the air purification unit can be associated with an audio-video system that is connectable to the internet. Such a video display system can stream video and audio or can play stored and recorded video and audio. The video display screen can be in front of the exhaled air blocking surface. The front of the video display screen can be part, or all, of the exhaled air blocking surface. The video display screen can be located above the exhaled air catch basin. The video display screen can be part of an air purification unit. The video-audio system can be part of the air purification unit. The video audio system can be supported by the air purification unit.

In aspects, an air purification unit can comprise an infrared ("IR") sensor. The exhaled air collector can comprise an IR sensor. An air purification chamber can comprise an IR sensor. The IR sensor can determine, in aspects, a) if someone is sitting behind the seat with the air purification unit, and/or b) if an individual sitting in the seat behind the seat with the air purification unit has a body temperature above a certain threshold. By way of example only, if the IR sensor senses a temperature of, by way of example only, 98° F. or above, it can cause a speed of a fan or fans within or attached to one or more of the air purification unit, exhaled air collector, air suction intake, air suction conduit, and/or air purification chamber, to increase in velocity or cubic feet per minute. In addition, the IR sensor can cause the fan or fans of the air purification unit(s), air collector(s), and/or conduit (s) in or attached to the seats to the right and/or left of the seat directly in front to go to a higher CFM (cubic feet per minute of air flow). Thus, in certain embodiments, a fan or fans located within or attached to the air purification unit can operate at two or more different CFMs. Accordingly, in certain embodiments, a fan or fans located within or attached to the exhaled air collector can operate at two or more different CFMs. In certain embodiments a fan or fans located within or attached to the air purification chamber can operate at two or more different CFMs. In certain embodiments, a fan or fans located within or attached to a section or part of an air purification system or unit can operate at two or more different CFMs.

A networked air purification system that comprises a plurality of networked exhaled air collectors and/or air purification units that connect to one or more remote air purification chambers can comprise an IR sensor. The IR sensor can determine, in aspects, a) if someone is sitting behind the seat with the air purification unit, and/or b) if an individual sitting in the seat behind the seat with the air purification unit has a body temperature above a certain threshold. By way of example only, if the IR sensor senses a temperature of 98° F. or above it can cause speed of a fan within or attached to the air purification unit, and optionally fans associated with air purification units associated with seats to the right and/or left of the seat directly in front, to go to a higher CFM. Thus, in certain embodiments, the fan or fans located within or attached to the air purification unit can operate at two or more different CFMs.

In certain embodiments of the invention, the air purification unit can comprise a carbon dioxide ("$CO_2$") sensor. The exhaled air collector can comprise a $CO_2$ sensor. The air purification chamber can comprise a $CO_2$ sensor. The air purification system can comprise a $CO_2$ sensor. A higher the $CO_2$ level can indicate a lack of good air circulation within a multi-seated indoor venue. Depending upon the level of $CO_2$ measured, the $CO_2$ sensor can cause a fan's CFM to increase or decrease in CFM. The air purification unit, air purification chamber, and/or air purification system can comprise an ozone sensor and cause an alarm, alert, or notification if the level of ozone exceeds a preset threshold. The air purification unit can comprise a photosensor. The air purification system can comprise a photosensor. The photosensor can cause the level of brightness of an electronic display that is part of or attached to the unit to be altered if the light level of the multi-seated venue is turned down or up. In the case of a reduction of a light level within the venue, by way of example only, an indoor theater, the level of light brightness of the electronic display can be turned down automatically. The reverse can occur when the level of brightness of the indoor venue is turned up (by way of example only, during an intermission).

In certain embodiments of the invention, the air purification unit can comprise a photosensor. The exhaled air collector can comprise a photosensor. The air purification chamber can comprise a photosensor. In aspects, the photosensor can sense if a coat, garment, or other obstruction is covering the air purification unit, exhaled air collector, and/or air purification chamber, and can cause an alarm, alert, or notification to be activated. The alarm, alert, or notification can be a light, sound, and/or electronic message. In embodiments, the chair can comprise a cylinder located between each chair capable of housing a coat or other garment. The cylinder can be of a fixed diameter or can be expandable or collapsible.

In certain embodiments of the invention, two or more chairs, seats, or benches can comprise a ring or cylinder or other device therebetween capable of housing or securing a garment or garments. The ring, cylinder, or other device can be collapsible. The ring, cylinder, or other device can be expandable. The location can be such that the garment can be positioned or stored between the two chairs so not to cover the exhaled air collector on or in the back of the chair, seat, or bench.

Figure 29:
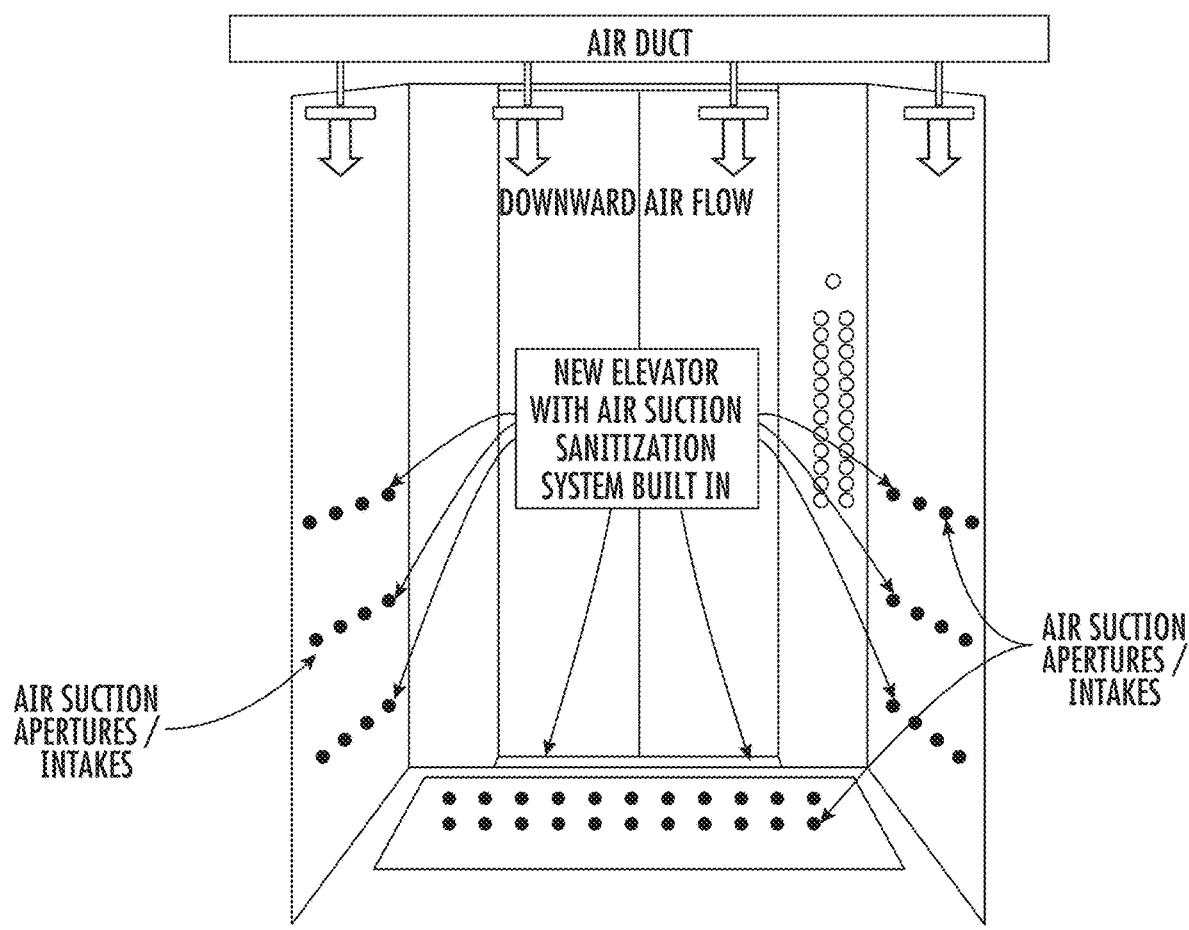
FIG. 29 is a schematic showing aspects of an air purification system as described herein being built or manufactured into an elevator car.

In certain embodiments of the invention, a chair, seat, or bench can comprise side protectors that can be raised or lowered and positioned between individuals that are sitting next to each other. (See FIG. 29.) A side protector can be transparent. The side protector can reduce exhaled air spread from individuals sitting in adjacent seats. A side protector can comprise a speaker or other electronic component that can enhance one's sensatory experience within, by way of example only, a theater or vehicle. A side protector can be made of a flexible material, such as by way of example only, plastic, rubber, or foam. (See FIG. 29, showing as an example the interior of an aircraft cabin including side protectors, shown when in use and as lowered when not in use. In aspects, air suction apertures in the back of the seats connect to a remote air purification system or air purification chamber. Downward air flow is also shown as described elsewhere in this application.)

A separate air handling system that provides overhead airflow working in concert with the air purification system can include that of an air dehumidifier. De-humidified air can decrease the time and distance a pathogen can remain/float in the air, or travel within the air. The air purification system can comprise one or more sensors including, by way of example only, acoustic, infrared, thermal, pressure, and/or accelerometer, as well as an anemometer to identify where individuals are seated within a multi-seated venue and/or assist in determining one or more of the air: volume, trajectory, suction force, and/or humidity percentage, for the air suction air sterilization system (including that of the overhead air flow). These sensors can then help direct overhead downward air flow towards and in front of the seated individual, thus assisting to move the exhaled air of that individual towards the exhaled air collector(s) associated with the chair or seat or bench in front of such seated individual. The sensors can determine if an individual is running a fever and adjust to a higher level the air suction force, the air suction force of an air suction aperture in front of such individual, and/or increase the overhead air flow directed at or in front of such air suction aperture. One or more sensors can determine if an individual coughed or sneezed and if so, adjust a suction force to a higher level and/or adjust a suction force to a higher level of an air suction aperture in front of such individual, and/or increase the overhead air flow directed at or in front of an exhaled air collector or air suction aperture. Artificial Intelligence can be employed to assist in learning the most efficient positioning of overhead air flow in terms of one or more of volume, velocity, trajectory, and/or humidity percentage. A computer system can be employed to help coordinate the amount of air suction or blowing force within one or more of an air suction aperture(s), an air purification unit, aspects of an air purification unit as described herein, an air purification system as described herein, and/or the overhead air flow. In certain embodiments, the air purification system (including the associated separate or integrated overhead air flow system) can be established to have a certain predetermined one or more of air velocity, volume, trajectory, suction force, and/or humidity percentage; thus, in aspects, not utilizing sensors or a CPU. However, in other embodiments, the air suction air sterilization system (including the associated separate or integrated overhead air flow system) utilizes sensors and a CPU to adjust overhead air flow, percentage of humidity, and a degree(s) of air suction. In certain cases, the coordination of the air suction with the overhead air flow is adjusted manually. In other cases, the coordination of the air suction with the overhead air flow is adjusted automatically. By coordination, in aspects, it is meant the adjustment of one or more of air velocity, volume, trajectory, suction force, and/or humidity percentage. Overhead air flow can include that of an air curtain directed at and/or in front of the where an individual is sitting.

Overhead air flow can be used to move or direct exhaled air into or at an air collector. The overhead air flow can be located above the seats within the venue. The overhead air flow can be, by way of example only, air nozzles, air ducts, or air curtain. The air nozzles or air ducts can be rotational around 360 degrees. The air nozzle or air ducts can be rotated or turned 360 degrees along the x, y, and/or z axes. The overhead air flow can be directed at and/or in front of an individual's exhaled air that is targeted. The overhead air flow can be directed at and/or in front of the exhaled air collector that is in front of where an individual is sitting. A targeted individual can be an individual sitting in a seat of a multi-seated venue. A targeted individual can be an individual standing in a multi-person venue. The targeting of the individual is to move all, or part of, the individual's exhaled air towards an exhaled air collector by way of overhead airflow. By way of example only, the adjustable overhead air nozzle(s) above the head of an individual sitting in a vehicle seat such as that of an aircraft, train, bus, or van can be aimed in the direction of an air collector positioned on the back of the seat directly in front of such individual.

Embodiments of the current invention can include exhaled air diagnosis, analysis, or screening in any indoor multi-seated venue where one seat is in front of another. This includes all kinds of vehicles and all kinds of theaters. In certain embodiments of the invention an exhaled air collector can connect to an exhaled air diagnostic device or analyzer or screener. In certain embodiments the exhaled air diagnostic device or analyzer or screener is located within or attached to the exhaled air catch basin. In certain embodiments the exhaled air diagnostic device or analyzer or screener is located within or attached to the exhaled air collector. In certain embodiments the exhaled air diagnostic device or analyzer or screener is located within or attached to the exhaled air purification unit. In certain embodiments the exhaled air diagnostic device or analyzer or screener is located within or attached to the exhaled air purification chamber. In certain embodiments the exhaled air diagnostic device or analyzer or screener can be positioned on, in, or in front of the back of a seat, chair, or bench. In certain embodiments, non-cleaned, non-filtered exhaled air from the exhaled air collector can be moved into the exhaled air diagnostic device or analyzer or screener. In certain embodiments, non-cleaned, non-filtered exhaled air from the exhaled air catch basin can be moved into the exhaled air diagnostic device or analyzer or screener. The movement can be by way of air suction or fan(s) pushing the exhaled air, or a combination of both. The exhaled air diagnostic device or analyzer or screener can comprise a plurality of sensors. These sensors can be, by way of example only, chemical sensor(s), nano-sensor(s), electrochemical sensor(s), gas sensor(s), and/or thermal sensor(s). The sensors can be used to analyze/screen/test for abnormal chemical concentrations of molecules or compounds found within the collected non-cleaned and/or non-filtered exhaled air of an individual. By way of example only, it is known that one's exhaled breath analysis can indicate the possible presence (or propensity) of the following conditions or health abnormalities: diabetes, multiple sclerosis, Parkinson disease, Alzheimer's, tuberculosis, chronic kidney disease, cancer of (lung, colon, breast, prostrate), asthma, stomach ulcers, COVID, bad breath, liver pathogenesis, and/or alcoholism. The exhaled air diagnostic device or analyzer or screener can comprise a communication module. Such a communication module can have the option to provide the individual whose exhaled air has been or is to be analyzed to approve or disapprove of having his or her exhaled air analyzed. Such a communication module can have the option to block any communication of the analysis of the individual's exhaled air. Such a communication module can have the option to approve the communication of the analysis of the individual's exhaled air. The communication module can provide wired or wireless communication to the individual whose exhaled air is being analyzed and/or to a third party. Software can provide for the ability to list those individuals who should be sent the exhaled air analysis. Such software can be shown on a video display screen prompting the individual to answer certain questions and optionally approve or disapprove of having his or her breath analyzed. Such communication can be that of an analysis of the individual's breath or an alert concerning a condition that was potentially identified to which the individual or the individual's doctor should be made aware of. The exhaled air diagnostic device or analyzer or screener can communicate wirelessly to a mobile device of the individual. Such a mobile device can be, by way of example only, a cell phone, tablet computer, laptop computer, smart watch, or other electronic device. The exhaled air diagnostic device or analyzer or screener can communicate to a video display screen located on or in the back of a seat. The exhaled air diagnostic device or analyzer or screener can communicate to a video display screen within or as part of an exhaled air collector. The exhaled air diagnostic device or analyzer or screener can comprise its own video display screen. In certain embodiments, the exhaled air diagnostic device or analyzer or screener can be independent of the exhaled air purification unit or system. In certain embodiments, the exhaled air diagnostic device or analyzer or screener can be located on, in, or separated from but in front of a back of a seat, chair, or bench within a multi-seated indoor venue. In certain embodiments the exhaled air collector can be that of a combination of a video display screen and its surrounding frame or housing. In this embodiment the air suction conduit can be an arm that secures or supports the video display screen. The video display screen can be part, or all, of the recessed exhaled air blocking surface. The exhaled air can be that of non-cleaned and/or non-filtered exhaled air. AI (artificial intelligence) and/or Machine Learning can be utilized to improve the analysis of the exhaled air and/or improve the screening and/or diagnosis accuracy. In certain embodiments of the invention, a passenger's or attendee's exhaled air can be subjected to microbe screening while the passenger or attendee is sitting in his or her seat. In certain embodiments of the invention, a passenger's or attendee's exhaled air can be subjected to microbe diagnosis and/or its existence while the passenger or attendee is sitting in his or her seat. In certain embodiments of the invention, a passengers or attendee's exhaled air can be subjected to viral diagnosis and/or its existence while the passenger or attendee is sitting in his or her seat. In certain embodiments of the invention, a passenger's or attendee's exhaled air can be subjected to germ diagnosis and/or its existence while the passenger or attendee is sitting in his or her seat. In certain embodiments of the invention, a passenger's or attendee's exhaled air can be subjected to coronavirus diagnosis and/or its existence while the passenger or attendee is sitting in his or her seat. In certain embodiments of the invention, a passenger's or attendee's exhaled air can be subjected to coronavirus diagnosis and/or its existence while the passenger or attendee is being transported in a vehicle or sitting in a theater. In certain embodiments of the invention, a passenger's or attendee's exhaled air can be subjected to microbe diagnosis and/or its existence while the passenger is being transported in a vehicle or the attendee is sitting in a theater. In certain embodiments of the invention, a passenger's or attendee's exhaled air can be subjected to viral diagnosis and/or its existence while the passenger being transported in a vehicle or the attendee is sitting in a theater. In certain embodiments of the invention, a passenger's or attendee's exhaled air can be subjected to germ diagnosis and/or its existence while the passenger is being transported in a vehicle or the attendee is sitting in a theater. Downward air flow from above the passenger's or attendee's seat can be used to assist in moving the passenger's or attendee's air into an exhaled air collector located in the back, top, or side of the seat in front of the passenger or attendee. The passenger's or attendee's exhaled air can be subjected to a microchip. The passenger's or attendee's exhaled air can be subjected to a gas sensor. The passenger's or attendee's exhaled air can be subjected to an electrochemical sensor. The passenger's or attendee's exhaled air can be subjected to a thermal sensor. The passenger's or attendee's exhaled air can be subjected to a spectrometer. The passenger's or attendee's exhaled air can be subjected to THz spectroscopy. The microchip, after being exposed to the passenger's or attendee's exhaled air, can be subjected to a spectrometer. A spectrometer can be part of the exhaled air purification system or exhaled air purification unit. A THz spectroscopy can be part of the exhaled air purification system or exhaled air purification unit. A computer device can be part of the exhaled air purification system or exhaled air purification unit. A communication device can be part of the air exhaled air purification system or exhaled air purification unit. In certain embodiments, an exhaled air purification system or exhaled air purification unit using diagnostics can inform an infected passenger or attendee they are infected with a virus or germ. In certain embodiments the air suction sterilization system using diagnostics can inform the captain of a vehicle that an infected passenger is traveling on their vehicle. In certain embodiments the exhaled air purification system or the exhaled air purification unit using diagnostics can inform the owner of the vehicle that an infected passenger is traveling on their vehicle. In certain embodiments the exhaled air purification system or the exhaled air purification unit using diagnostics can inform one of the owner, driver, pilot, and/or attendant of the vehicle that an infected passenger is traveling on their vehicle. In certain embodiments the exhaled air purification system or the exhaled air purification unit using diagnostics can inform one of the owner, driver, pilot, and/or attendant of the vehicle that an infected passenger is traveling on their vehicle and in which seat the infected passenger is sitting. The same can occur within a multi-seated theater in which an attendee is sitting, however in this case, by way of example only, theater management or a security guard may be informed.

Another embodiment of an invention disclosed herein is of an air sanitized elevator, wherein an elevator car comprises a plurality of air suction apertures or intakes and wherein the air suction apertures or intakes connect to a remote air purification chamber. The elevator car can comprise a façade wall or walls that comprise air suction apertures or intakes. In most, but not all cases, such a façade wall or walls are utilized when retrofitting an elevator car with such an air purification system and/or air purification unit, including, in cases, a remote air purification chamber. In still other embodiments where new elevator construction is utilized, the walls of the elevator can provide the location for the air suction apertures or intakes. In either the case of a façade wall(s) or a permanent wall(s) of the elevator car, the location of the air suction apertures or intakes can be below the midline height of the elevator façade wall(s) or permanent wall(s). The elevator car can comprise downward air flow from the ceiling downward. The elevator car can comprise air flow upward into the ceiling. The elevator car can comprise air suction apertures or intakes on multiple walls. The elevator can comprise air suction apertures or intakes on the floor. The elevator can comprise air suction apertures or intakes on the ceiling. The air purification and/or air handling equipment can be located at the bottom/underneath portion of the elevator car. The air purification and/or air handling equipment can be located remotely to/from the elevator car. The air purification and/or air handling equipment can be located under the floor of the elevator car. The air purification and/or air handling equipment can be located behind a wall of the elevator car. The air purification and/or air handling equipment can be located above the ceiling of the elevator car. The downward air flow within the elevator can be from an air curtain. In aspects, the downward air flow can be from one or more fans, nozzles, vents, ducts, or holes. The downward air flow can be directional and controlled. In this embodiment the downward air flow moves the exhaled air of one or more individuals within the elevator car downward towards the floor. In certain embodiments the air suction apertures or intakes located in the floor or the lower part of the side walls around the floor can then move by way of suction the exhaled air out of the elevator car and to a location where it can be cleaned and/or filtered and then recirculated back into the elevator car. In certain embodiments the air suction apertures or intakes located in the floor or the lower part of the side walls around the floor can then move by way of suction the exhaled air out of the elevator and to a location where it can be cleaned and/or filtered and then exhausted into the outside environment. In certain embodiments the air suction apertures or intakes located in the floor or the lower part of the side walls around the floor can then move by way of suction the exhaled air out of the elevator where it can be exhausted into the outside environment.

Now turning to additional Figures, FIG. 1 shows an embodiment of an air purification unit integrated within or attached to the back of a chair as described herein. The figure shows the back of the chair 1001, the exhaled air collector 1002, the recessed exhaled air surface blocking surface 1003 at the back of the collector, and the air purification chamber 1004, which in this case is adjacent and connected to the exhaled air collector. In this particular embodiment, the air purification chamber includes a section for UVC light/radiated air purification 1005. This embodiment also shows a trap guide 1006 for trapping objects, including the trap for catching objects 1007.

Figure 2:
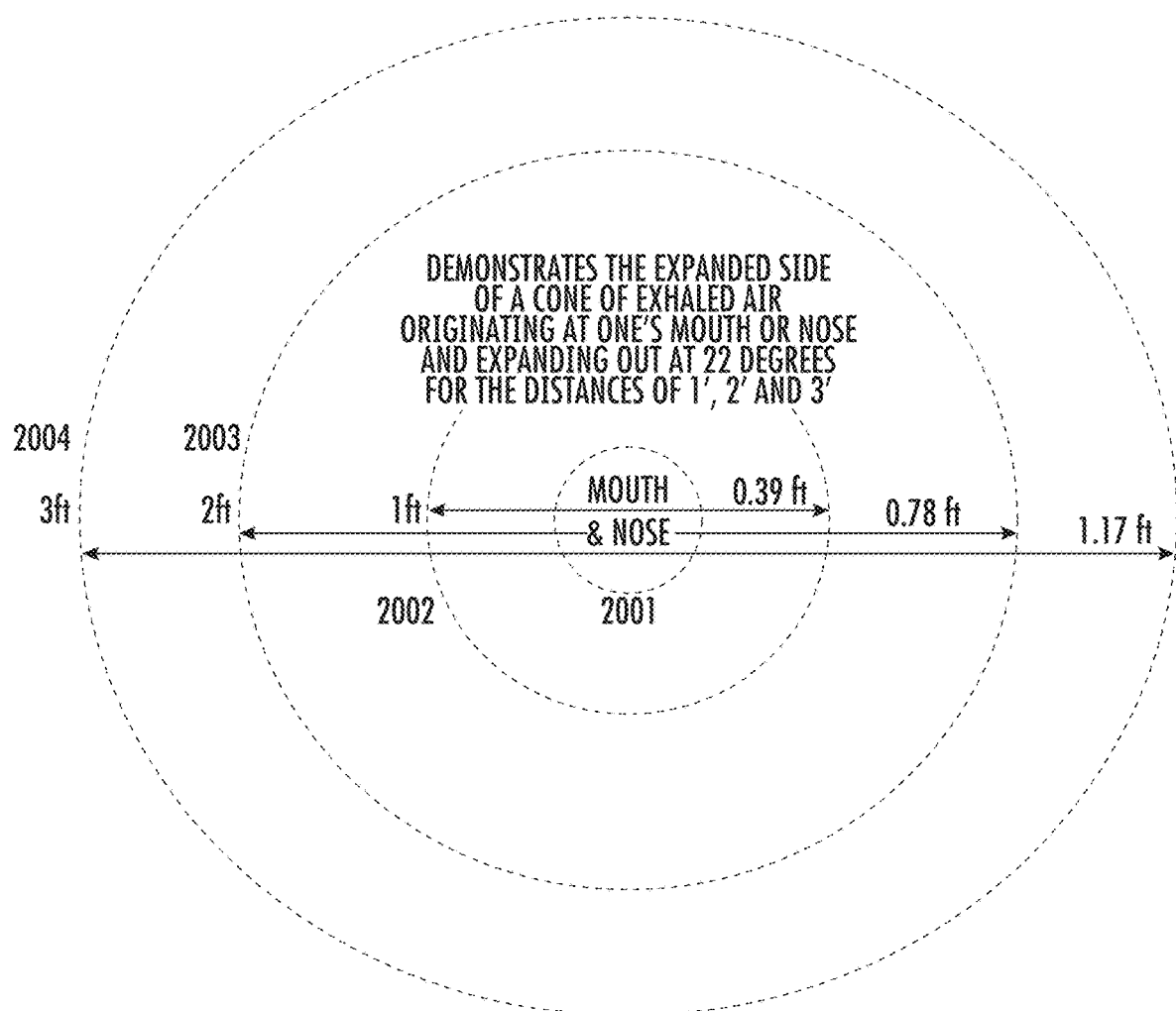
FIG. 2 is a schematic demonstrating the expanded side of a cone of exhaled air originating at one's mouth or nose having originating dimension of 55 mm in diameter and expanding out at 22 degrees for the distances of one foot, two feet, and three feet, assuming a 22 degrees enlarging cone of exhaled air.

FIG. 2 shows a cone of exhaled air, and demonstrates the expanded side of a cone of exhaled air originating a human's mouth or nose 2001 and expanding out at 22 degrees for the distance of 1 foot 2002, 2 feet 2003, and 3 feet 2004. This figure is not to scale and assumes a 22 degrees enlarging cone of exhaled air.

Figure 3:
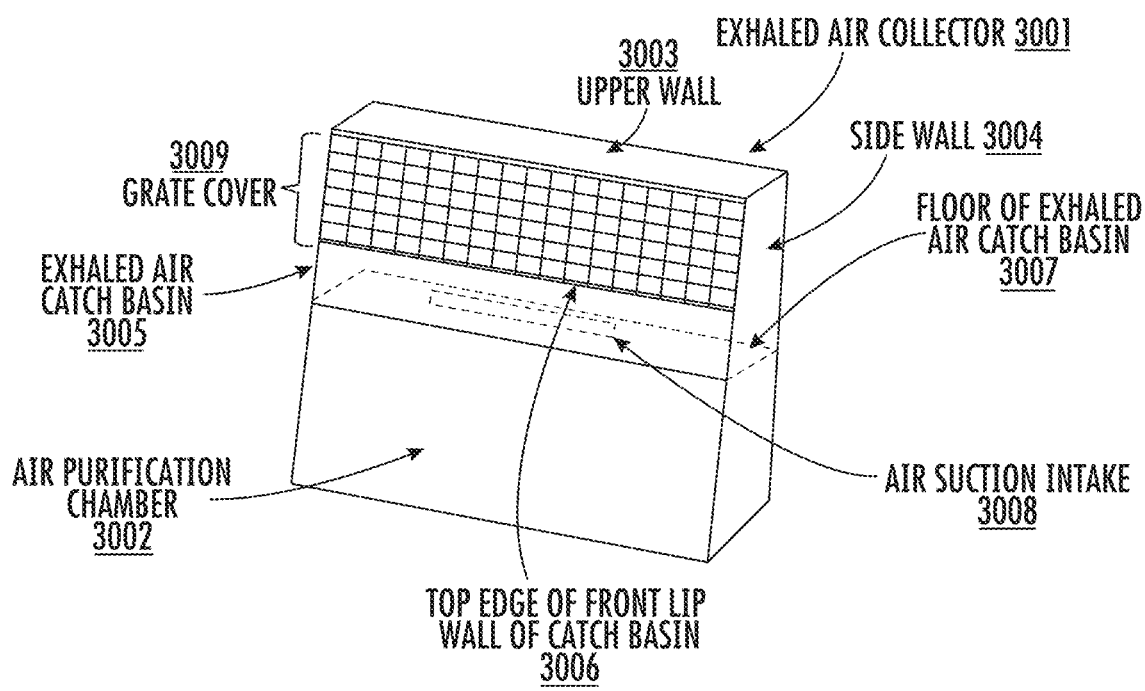
FIG. 3 is a schematic of a possible embodiment according to the present invention showing an air purification unit.

FIG. 3 shows a possible embodiment of an air purification unit as described herein. This embodiment shows an exhaled air collector 3001 directly adjacent and connected to the air purification chamber 3002. In this case, the air collector includes an upper wall 3003 and side wall 3004. It also includes an exhaled air catch basin 3005 (see top edge of front lip 3006 of exhaled air catch basin) and the floor of the exhaled air basin 3007 shows an integrated air suction intake 3008 that leads to the air purification chamber 3002. In this example, the unit includes a grate cover 3009, for example so that objects to not get inserted into the air purification unit.

Figure 4:
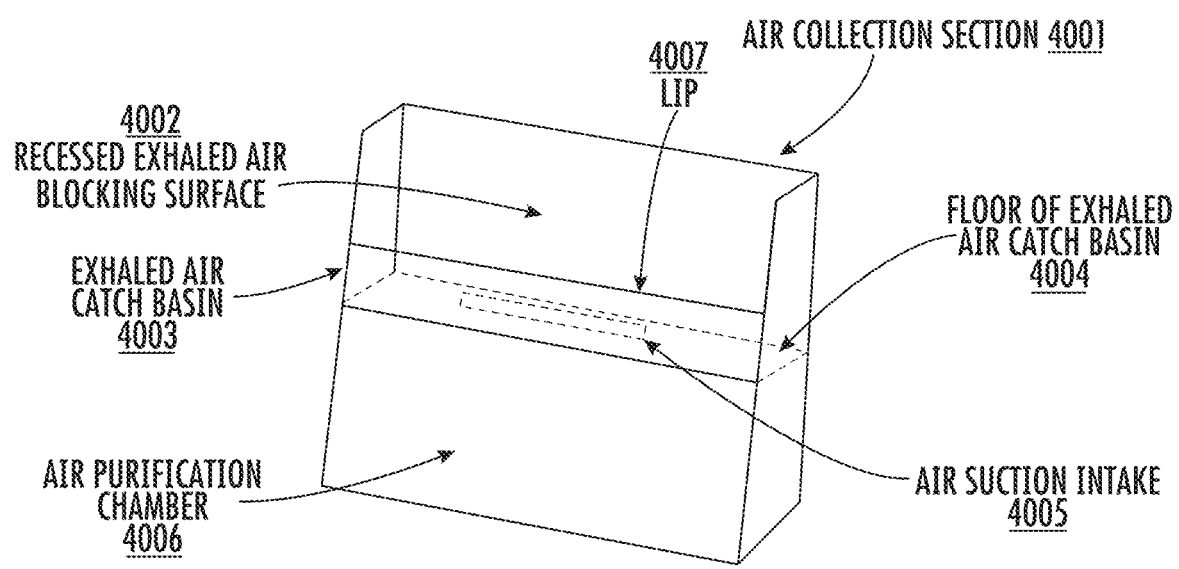
FIG. 4 is a schematic of a possible embodiment according to the present invention showing an air purification unit.

FIG. 4 shows another embodiment of the air purification unit. In this embodiment the air collection section 4001 does not have a top wall or a grate like in FIG. 3. It does have a recessed exhaled air blocking surface 4002 and an exhaled air catch basin 4003 (see top edge of front lip of exhaled air catch basin 4007). At the floor of the exhaled air catch basin 4004 is an air suction intake 4005 that leads to the air purification chamber 4006.

Figure 5:
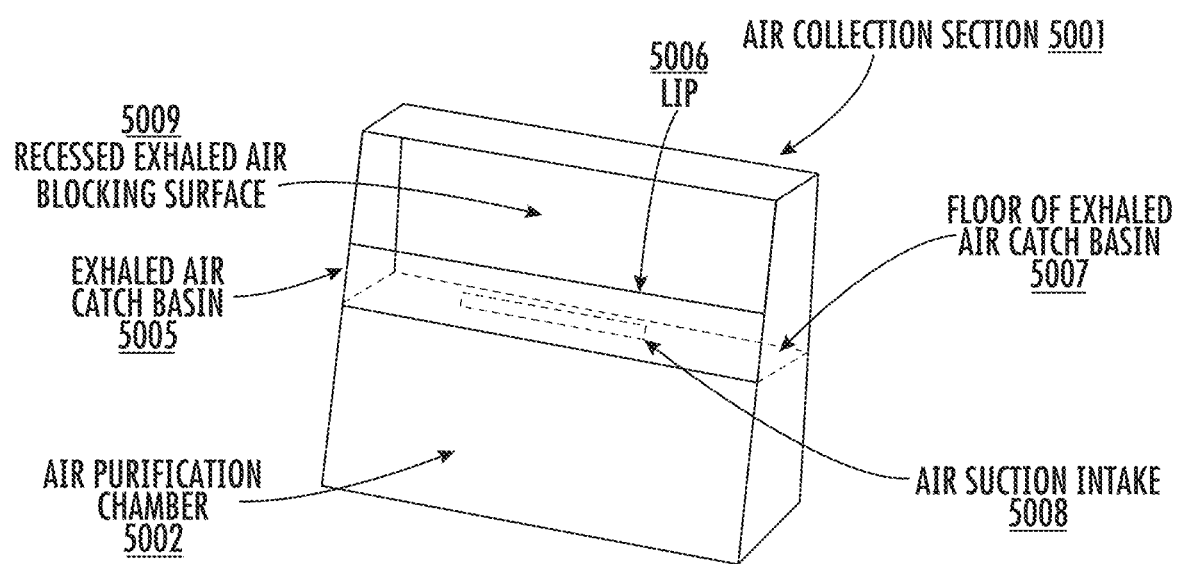
FIG. 5 is a schematic of a possible embodiment according to the present invention showing aspects of an air purification unit.

FIG. 5 shows a possible embodiment of an air purification unit as described herein. This embodiment shows an exhaled air collector 5001 directly adjacent and connected to the air purification chamber 5002. In this case, the air collector includes an upper wall and side wall, and a recessed exhaled air blocking surface 5009. It also includes an exhaled air catch basin 5005 (see top edge of front lip 5006 of exhaled air catch basin) and the floor of the exhaled air basin 5007 shows an integrated air suction intake 5008 that leads to the air purification chamber 5002.

Figure 6:
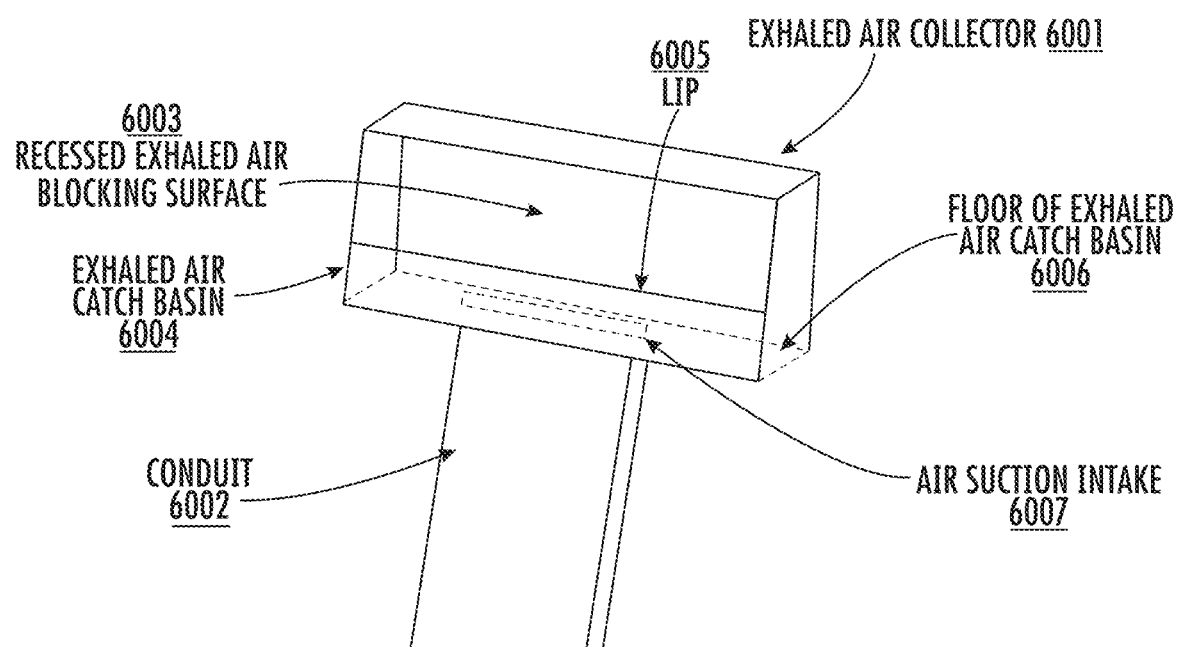
FIG. 6 is a schematic of a possible embodiment according to the present invention showing aspects of an air purification unit.

FIG. 6 shows a possible embodiment of an the exhaled air collector connected to a conduit. This embodiment shows an exhaled air collector 6001 directly connected to the a conduit 6002. In this case, the air collector includes an upper wall and side wall, and a recessed exhaled air blocking surface 6003. It also includes an exhaled air catch basin 6004 (see top edge of front lip 6005 of exhaled air catch basin) and the floor of the exhaled air basin 6006 shows an integrated air suction intake 6007 that leads to the conduit 6002. In aspects, the conduit can lead to a remote air purification chamber, the floor and/or intake vents near the floor of an aircraft cabin, an HVAC unit, an air purification or handling system, out of a venue, or other examples as described herein. In aspects, the conduit can be networked with other conduits, air purification units, air collectors, or other aspects of an air purification unit, and, in cases, can lead to one or more air purification chambers.

Figures 7A, 7B, 7C:
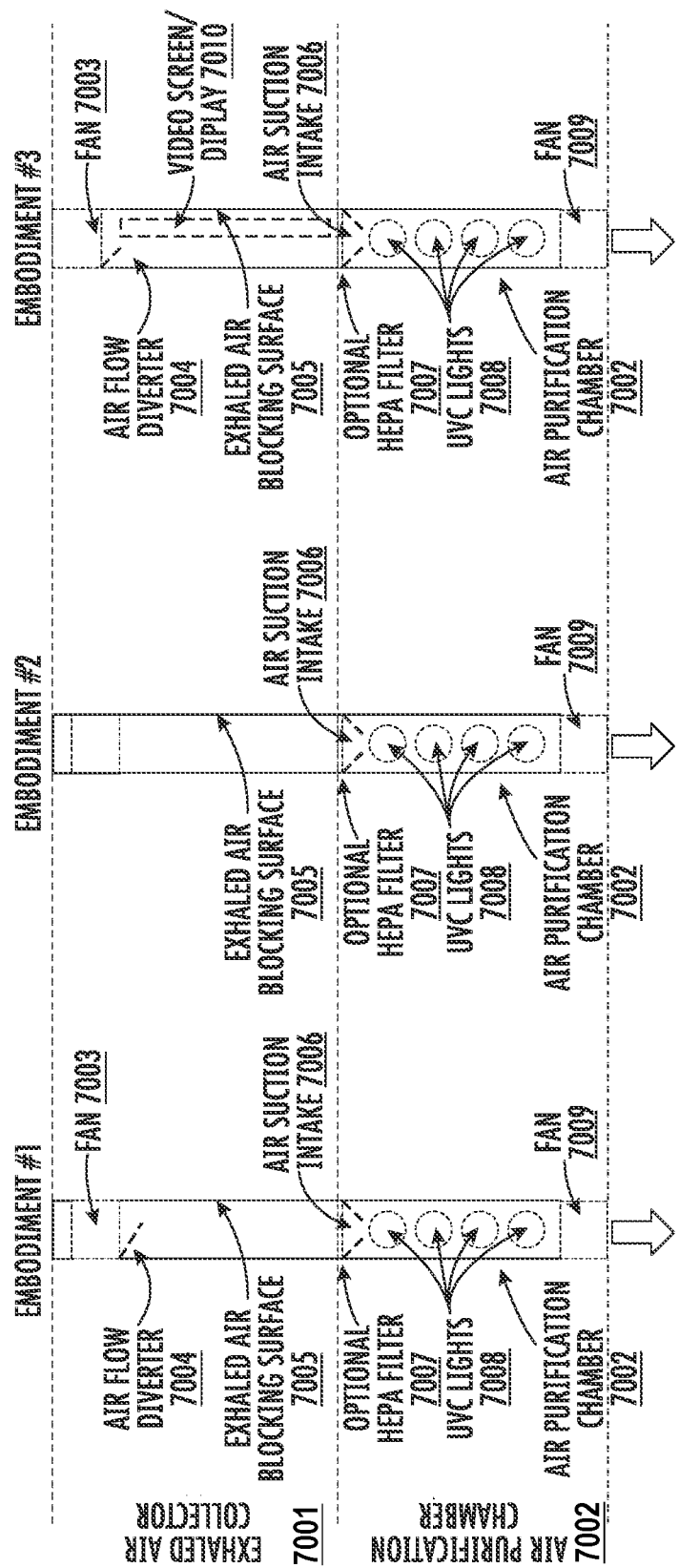
FIGS. 7A, 7B, and 7C are schematics of possible embodiments according to the present invention showing aspects of an air purification unit.

FIGS. 7A, 7B, and 7C show different embodiments of an air purification unit comprising an exhaled air collector 7001 and an air purification chamber 7002. In FIG. 7A, an embodiment is shown with a fan 7003 at the top of or above the air purification unit, which in aspects pushes, blows, and/or directs exhaled air downward and/or towards the exhaled air blocking surface 7005. FIG. 7A also includes an air flow diverter 7004 to divert exhaled or blown air downward and/or towards the exhaled air blocking surface 7005, which leads to an air suction intake 7006 and to the air purification chamber 7002, which in this case shows an optional HEPA filter(s) 7007 and an optional UVC light(s) 7008. This embodiment also shows a fan 7009 under, beneath, or incorporated in the air purification chamber that suctions air downwards and/or pushes air out of the air purification chamber. FIG. 7B shows a similar embodiment to FIG. 7A but wherein a fan is not located at the top of or above the air purification unit. In the case of FIG. 7B, air flow, gravity, and/or the air suction intake can move, divert, direct, and/or suction air into the air purification chamber.

FIG. 7C shows a similar embodiment to FIG. 7A but wherein the exhaled air collector comprises a video screen/display 7010. In aspects, the exhaled air blocking surface can be the video screen/display or the video screen/display can be in front of the exhaled air blocking surface.

Figure 8:
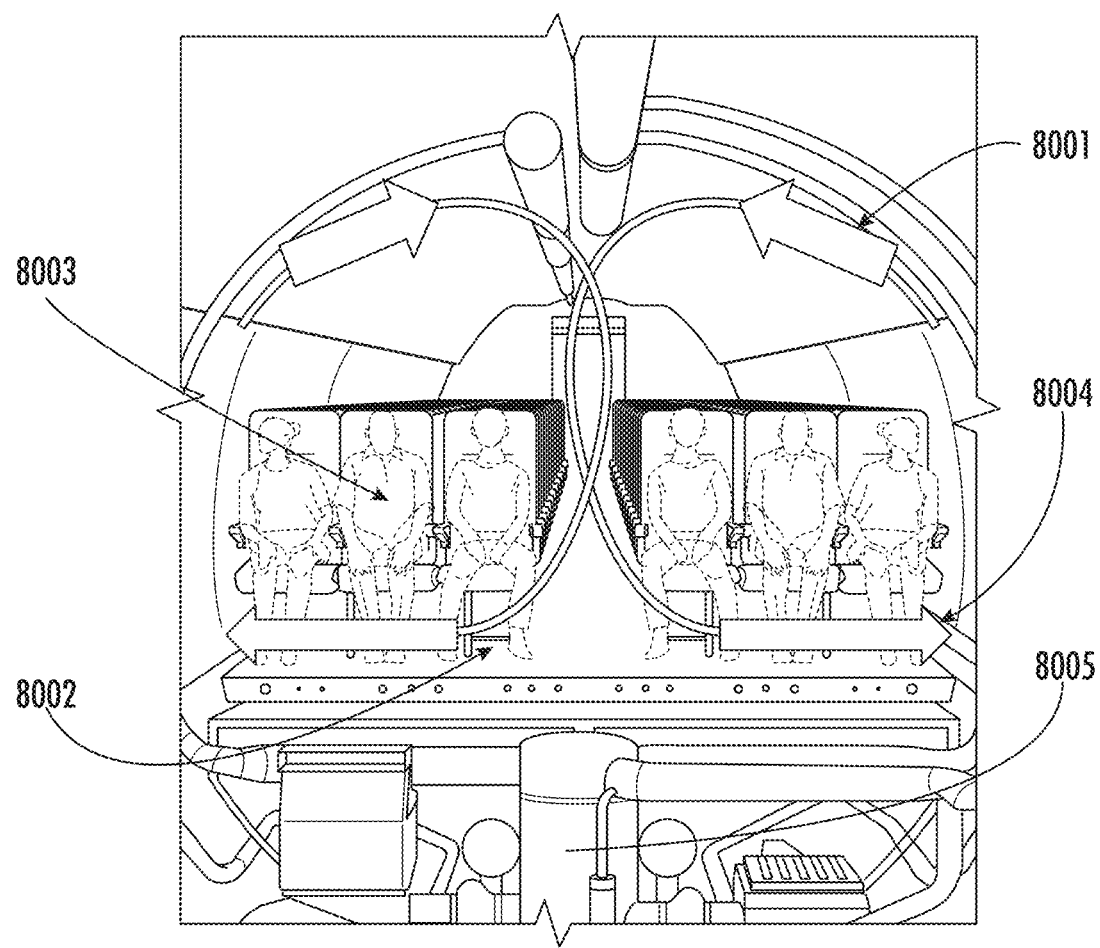
FIG. 8 is a schematic showing air flow current in an aircraft cabin.

FIG. 8 shows a typical air circulation configuration in the cabin of an aircraft. Air comes from or is pumped or is blown from at or near the ceiling of the aircraft cabin 8001 and then goes towards the floor of the aircraft cabin 8002, in cases carrying exhaled air from cabin passengers 8003 where that air is sucked into vents in or near the floor of the aircraft 8004. It then passes to the aircraft's air purification or handling system 8005 and then the purified or handled air is returned to the ceiling of the air and the cycle begins again. In some cases air from the cabin is released from the aircraft. This system or similar systems as understood by one of skill in the art is in cases used by other vehicles, such as trains, cars, buses, trucks, etc.

Figure 9:
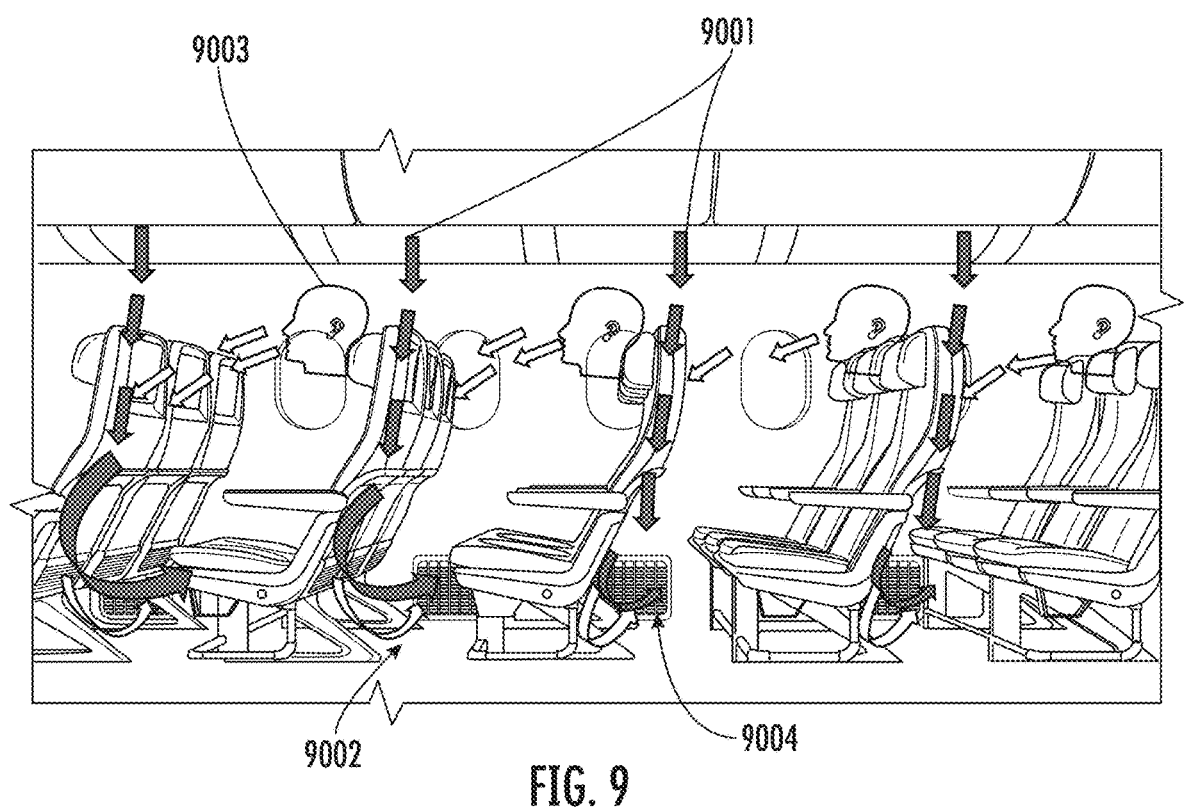
FIG. 9 is a schematic showing air flow current in an aircraft cabin and aspects of an air purification unit/system as described herein.
Figure 10:
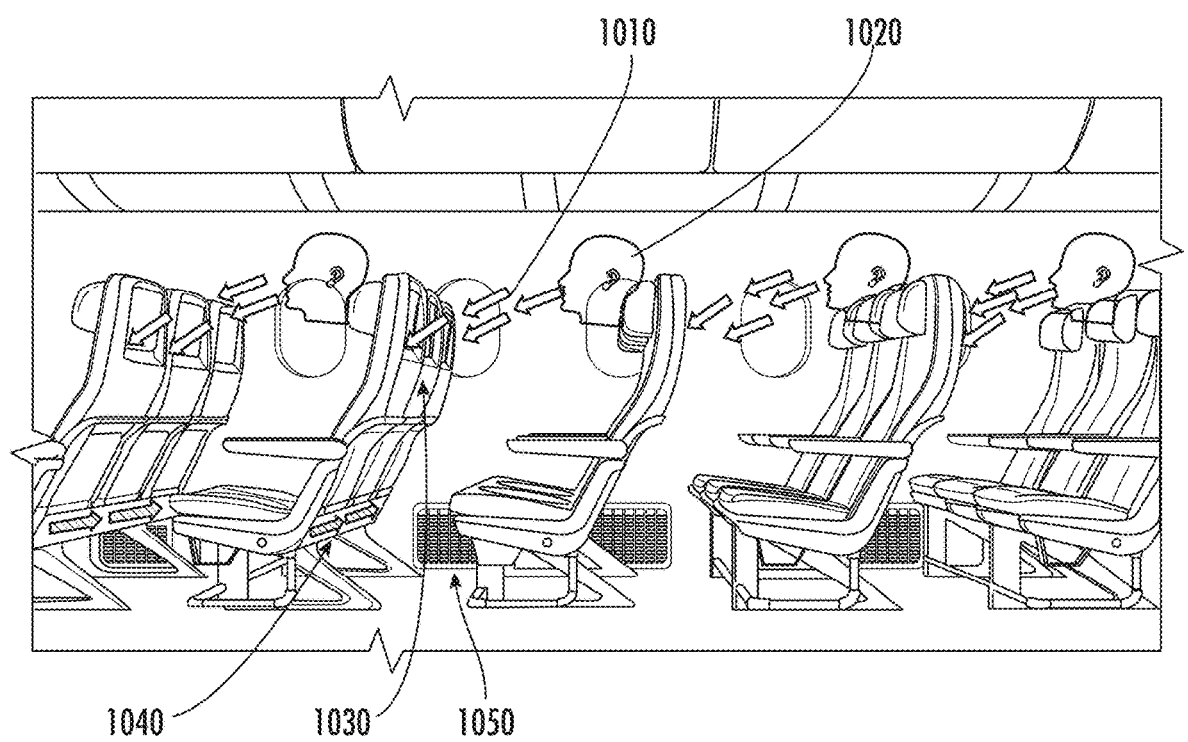
FIG. 10 is a schematic showing air flow current in an aircraft cabin and aspects of an air purification unit/system as described herein.

Such a system is similarly shown in FIG. 9, wherein air comes from or is pumped or blown from the ceiling of the aircraft 9001, such as vents or nozzles. The air from the ceiling moves exhaled air from passengers 9003 in the aircraft cabin towards the floor of the aircraft 9002 where the air from the aircraft cabin and the exhaled air is then captured by vents at or near the floor of the aircraft cabin 9004.

Figure 11:
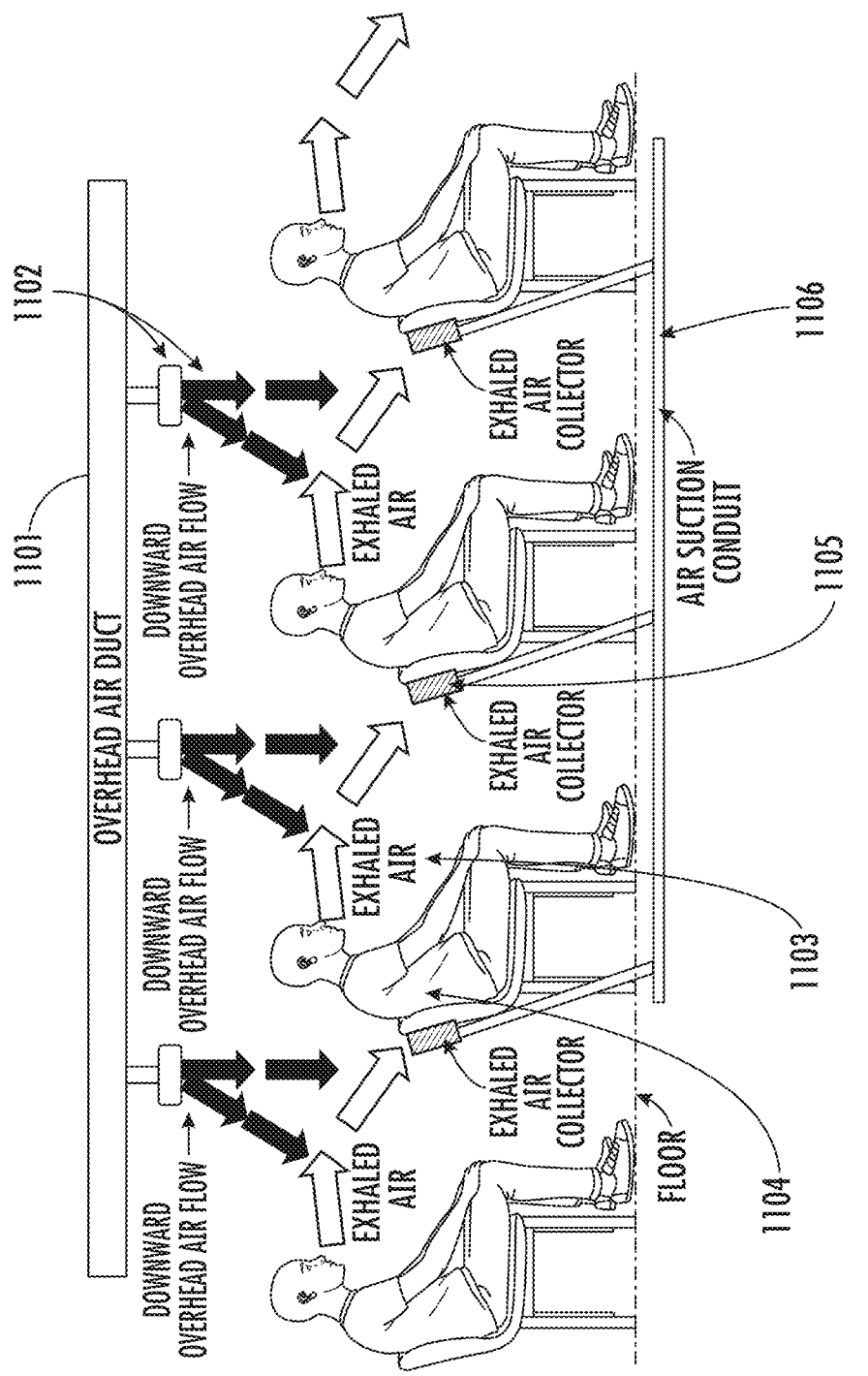
FIG. 11 is a schematic showing aspects of an air purification unit as described herein.
Figure 12:
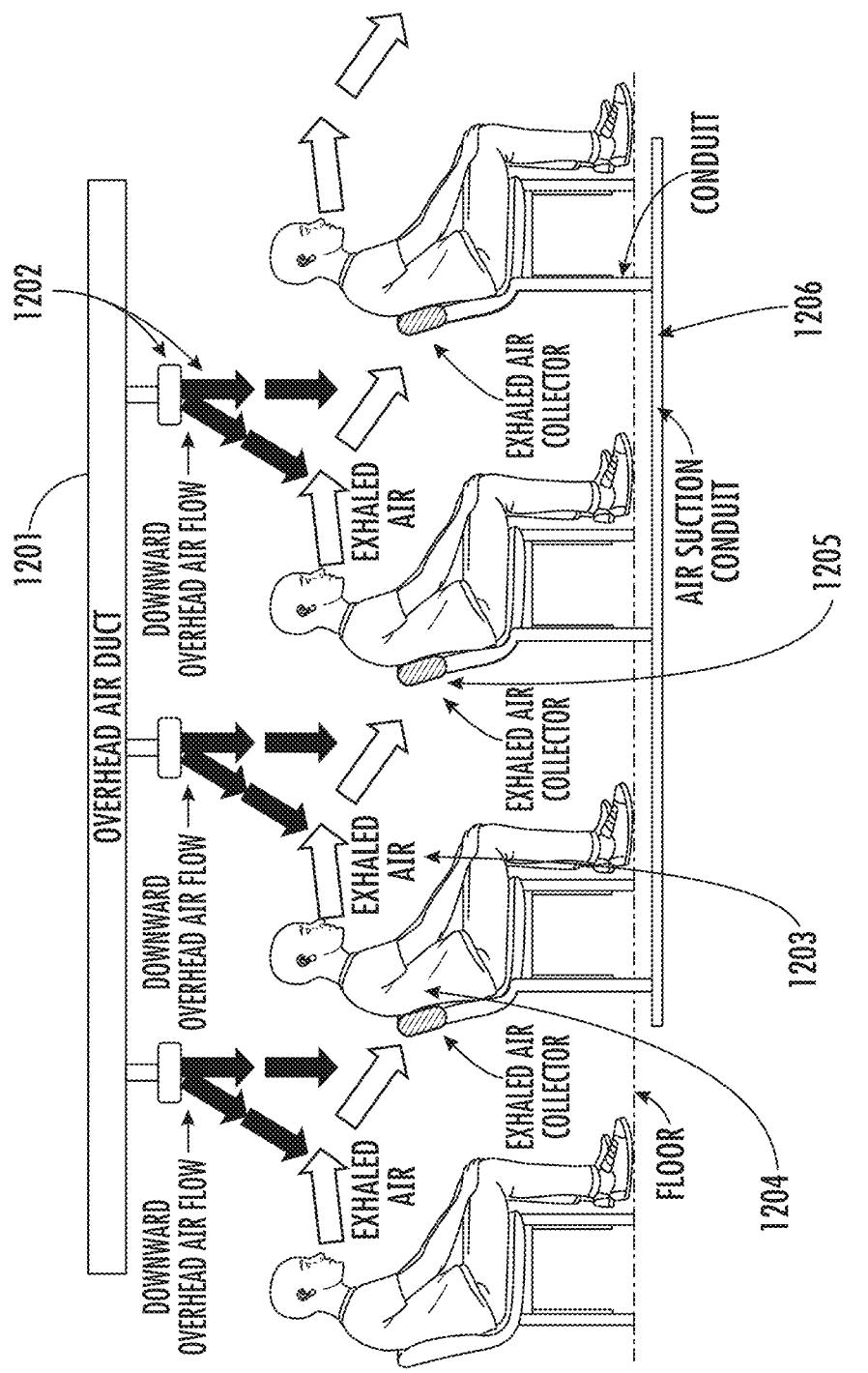
FIG. 12 is a schematic showing aspects of an air purification unit as described herein.
Figure 13:
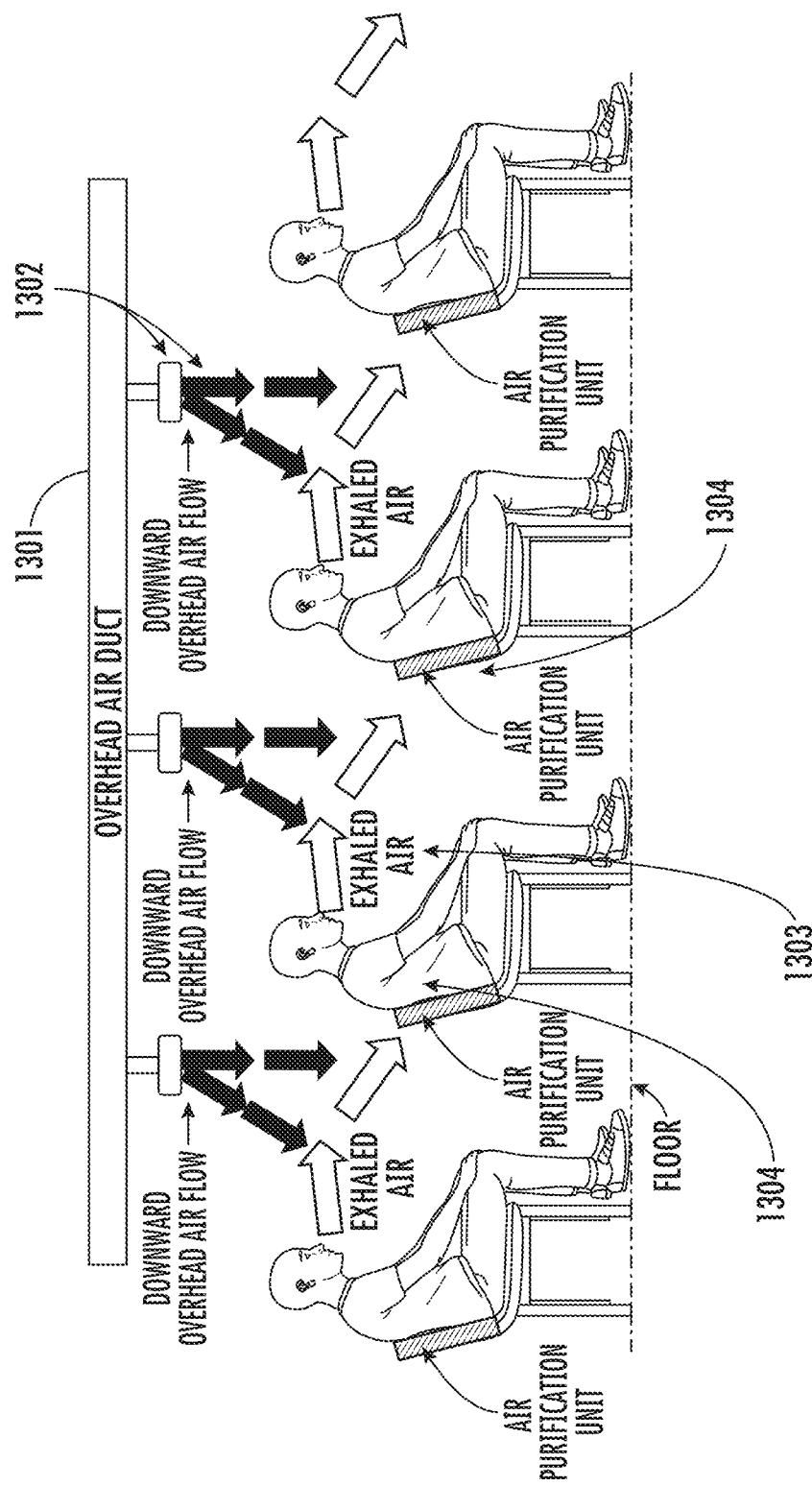
FIG. 13 is a schematic showing aspects of an air purification unit as described herein.
Figure 14:
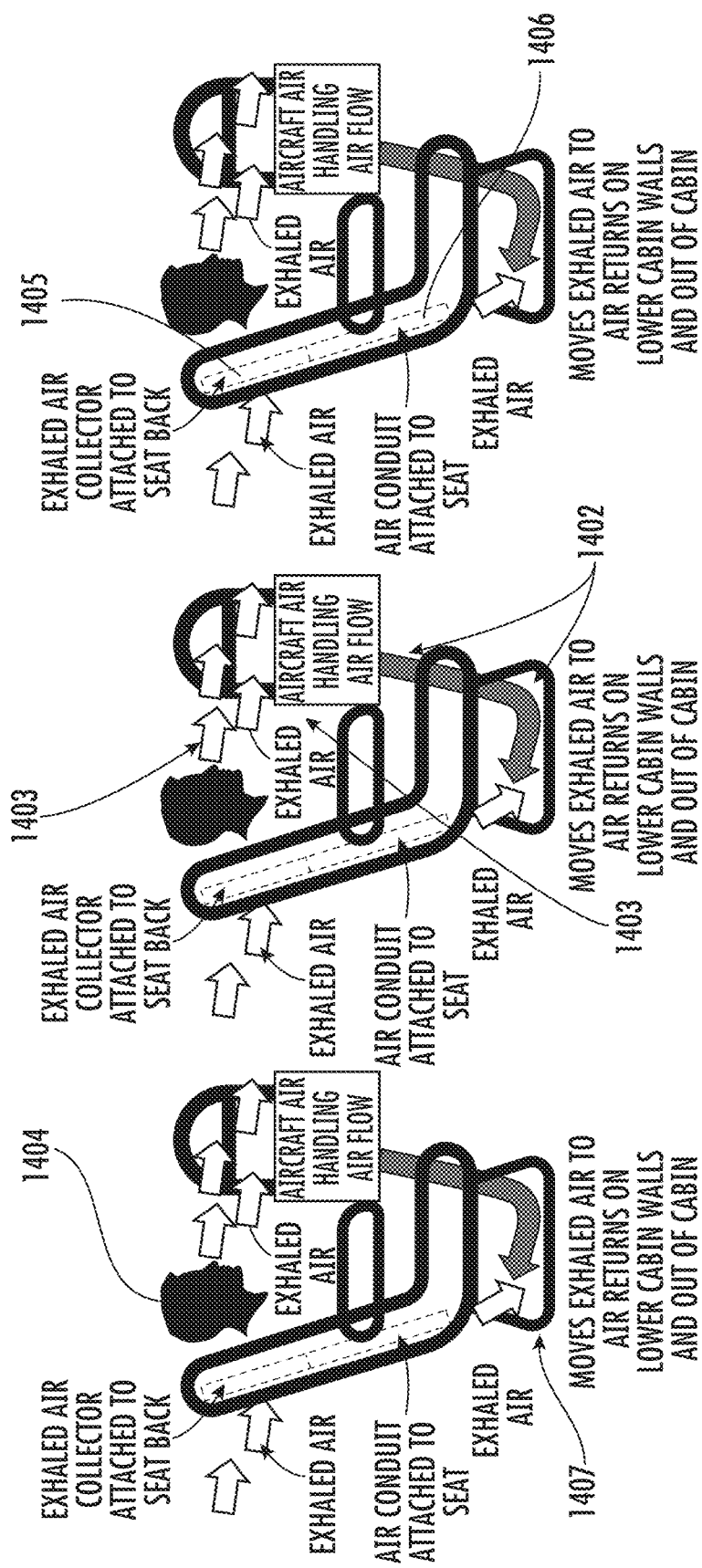
FIG. 14 is a schematic showing aspects of an air purification unit as described herein.
Figure 15:
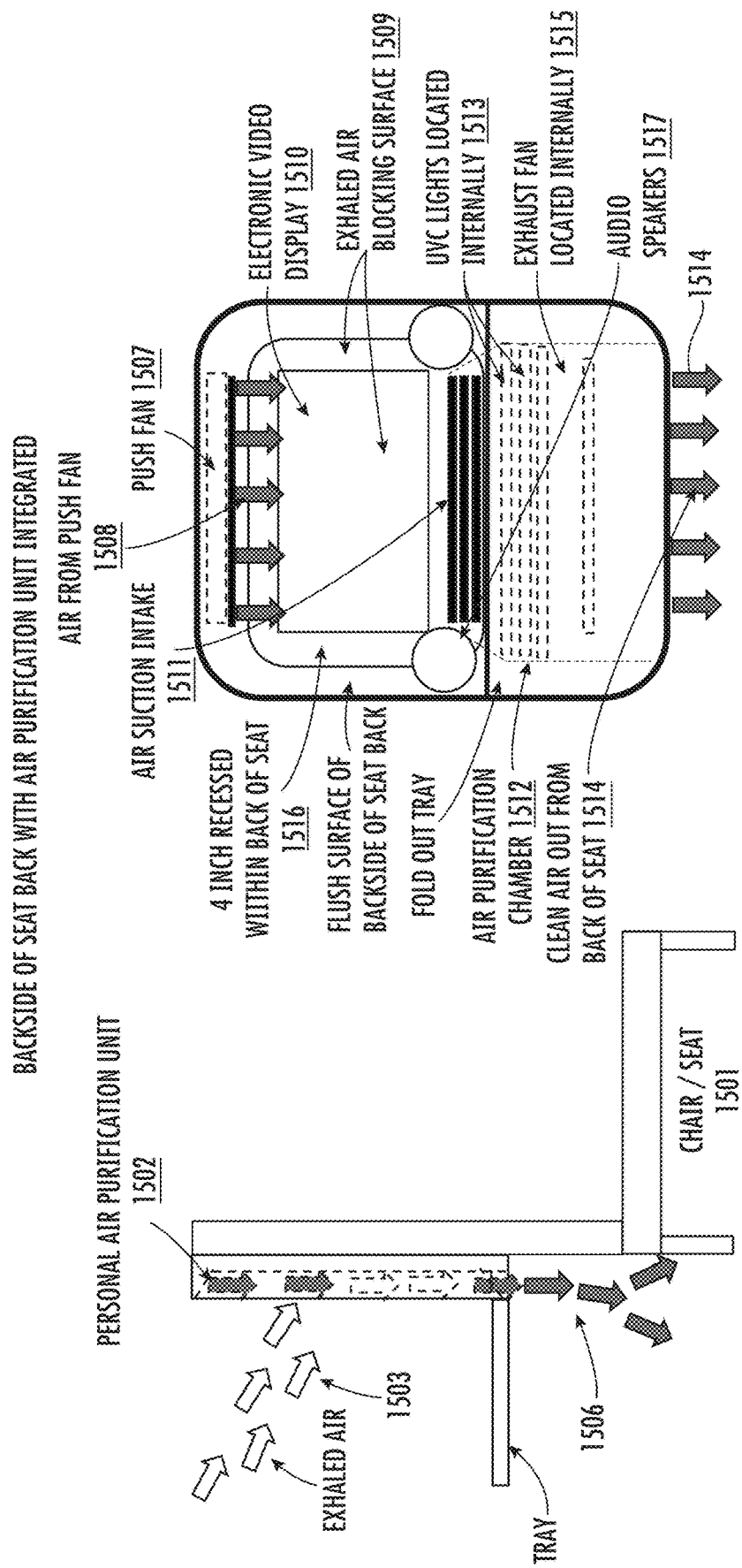
FIGS. 15A and 15B are schematics showing aspects of an air purification unit as described herein.
Figure 16:
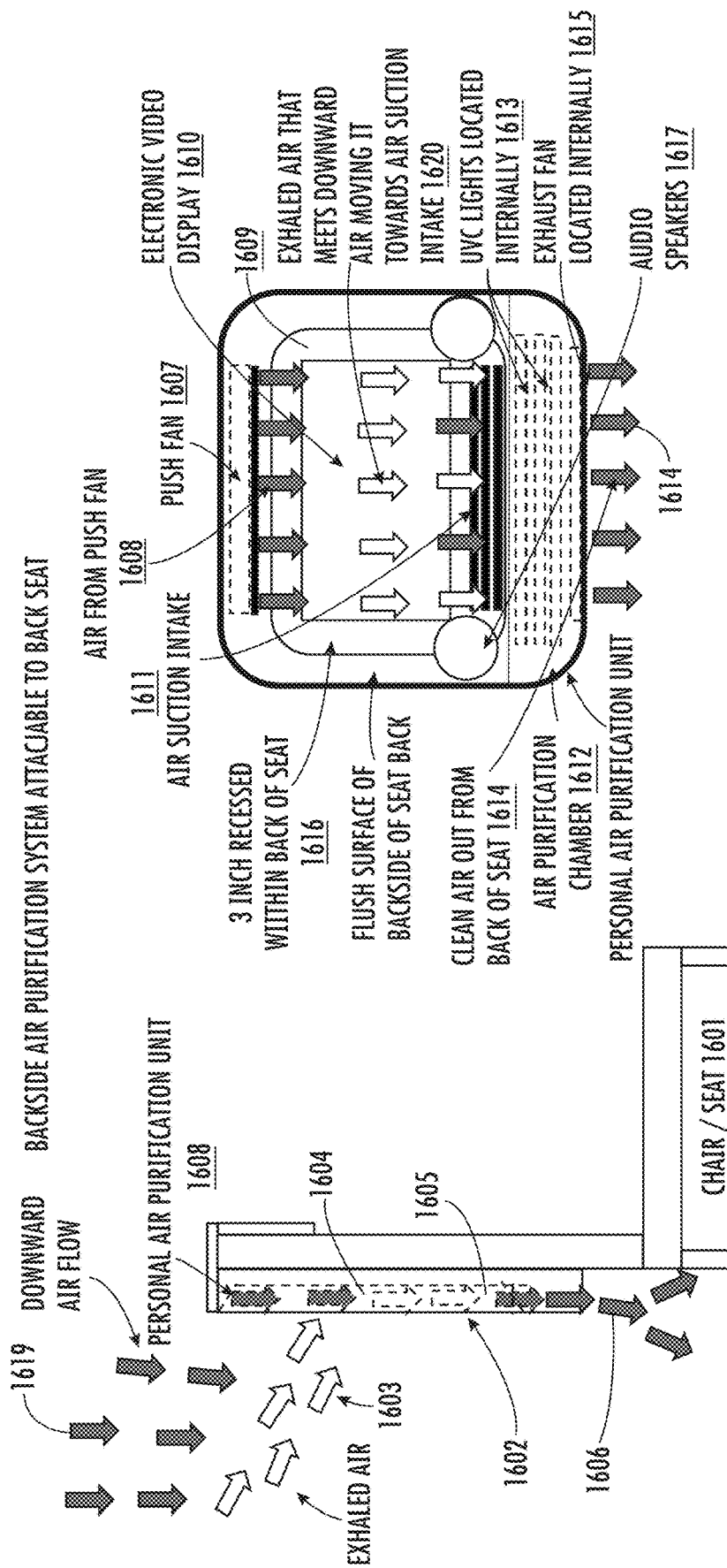
FIGS. 16A and 16B are schematics showing aspects of an air purification unit as described herein.

FIG. 11 shows an embodiment such as in a vehicle, wherein an overhead air duct 1101 creates downward overhead air flow 1102 which moves exhaled air 1103 from a passenger 1104 to an air suction intake 1105 and then to an air suction conduit 1106, which moves the exhaled air to a remote air purification chamber, an air handling unit, an HVAC, and/or to a different environment. FIG. 12 shows an embodiment such as in a vehicle, wherein an overhead air duct 1201 creates downward overhead air flow 1202 which moves exhaled air 1203 from a passenger 1204 to an exhaled air collector 1205 as described herein and then to an air suction conduit 1206—such as by way of or through a conduit connecting the exhaled air collector 1205 to the air suction conduit 1206—which air suction conduit 1206 moves the exhaled air to a remote air purification chamber, an air handling unit, an HVAC, and/or to a different environment. In this case the exhaled air collector can be integrated within or attached to the seat/chair. FIG. 13 shows an embodiment such as in a vehicle, wherein an overhead air duct 1301 creates downward overhead air flow 1302 which moves exhaled air 1303 from a passenger 1304 to an air purification 1305 as described herein, wherein the air purification can be integrated within or attached to the seat/chair, including removeably attached so that the air purification unit can be removed, attached, and replaced. In this case the air purification unit can be mobile and taken or carried from one place to another. FIG. 14 shows an embodiment such as in a vehicle, wherein downward moving air flow 1402 from the aircraft's air handling system air flow moves exhaled air 1403 from a passenger 1404 to an exhaled air collector 1405 attached to the seat and then to an air conduit attached to the seat 1406, which moves the exhaled air to a vent at or near the floor of the cabin 1407, such as in the lower cabin walls, which then takes the exhaled air and aircraft's downward moving air flow/current out of the cabin. In aspects, this air is then moved to a remote air purification chamber, an air handling unit, an HVAC, and/or to a different environment.

FIG. 15A shows an embodiment wherein the backside of the seat 1501 integrates an air purification unit 1502. In this example, exhaled air 1503 is collected by an exhaled air collector 1504, cleaned by an air purification chamber 1505, and then released 1506 from the air purification unit. The air purification unit could also be releasably attached to the back side of the seat, such as by hooking onto the seat with a hooking mechanism, hook, fastener, Velcro, snap, button, zipper, clasp, or other mechanism for attaching the air purification to the back of seat. FIG. 15B shows a fan 1507 pushing air downwards 1508 over the exhaled air blocking 1509, which in cases comprises an electronic video display screen 1510, and then the collected exhaled air is pushed down and/or suctioned into an air suction intake 1511. In this embodiment, that air passes directly to an air purification chamber 1512, where it is cleaned, such as by filters or UVC lights 1513 located internally within the air purification chamber, and the cleaned air 1514 is then released from the air purification unit, such as by an exhaust fan 1515 located internally or externally with respect to the air purification chamber. In aspects, the exhaled air blocking surface is recessed 4 inches within the back of the seat 1516. In this embodiment audio speakers 1517 are also shown. In aspects, the exhaled air blocking surface of the exhaled air collector can be recessed around 3 or 4 inches. The exhaled air blocking surface of the exhaled air collector can be recessed within a range of 0.25 inches to 12 inches. Aspects may include a tray, such as a hidden tray. In aspects, exhaled air is pushed downwards by a vehicle's air handling or purification unit, overhead vents, fans, or nozzles, and/or fan(s) above or on top of the air purification unit or exhaled air collector. In some cases, no overhead air flow or current is used, such as the aforementioned vehicle's air handling or purification unit, overhead vents, fans or nozzles, and/or fan(s) above or on top of the air purification unit or exhaled air collector. In such cases, gravity or the natural direction of exhaled air is used, such as when the exhaled air hits the exhaled air blocking surface of the exhaled air collector it naturally heads downward to the air suction intake; the air suction intake, in aspects, may also assist downward flow of the exhaled air towards the air suction intake and into, for example, a conduit or air purification chamber.

FIG. 16A shows an embodiment wherein the backside of the seat 1601 has an air purification unit 1602 attached, such as by hooking onto the seat with a hooking mechanism (e.g., 1618), hook, fastener, Velcro, snap, button, zipper, clasp, or other mechanism for attaching the air purification to the back of seat. In other embodiments, the air purification can be integrated within the back of the seat. In this example, exhaled air 1603 is pushed downward by downward air flow 1619, such as from a vent or nozzle in or near a vehicle ceiling (not pictured), is collected by an exhaled air collector 1604, cleaned by an air purification chamber 1605, and then released 1606 from the air purification unit. FIG. 16B shows a fan 1607 pushing air downwards 1608 over the exhaled air blocking 1609, which in cases comprises an electronic video display screen 1610. In this case, exhaled air meets downward moving air 1620 and moves exhaled air mixed with downward moving air to the air suction intake 1611 where it suctioned into an air suction intake 1611. In this embodiment, that air passes directly to an air purification chamber 1612, where it is cleaned, such as by filters or UVC lights 1613 located internally within the air purification chamber, and the cleaned air 1614 is then released from the air purification unit, such as by an exhaust fan 1615 located internally or externally with respect to the air purification chamber. In aspects, the exhaled air blocking surface is recessed 3 inches within the back of the seat 1616. In this embodiment audio speakers 1617 are also shown. In aspects, the exhaled air collector can be recessed around 3 or 4 inches. Aspects may include a tray, such as a hidden tray. In aspects, exhaled air is pushed downwards by a vehicle's air handling or purification unit, overhead vents, fans or nozzles, and/or fan(s) above or on top of the air purification unit or exhaled air collector. In some cases, no overhead air flow or current is used, such as the aforementioned vehicle's air handling or purification unit, overhead vents, fans or nozzles, and/or fan(s) above or on top of the air purification unit or exhaled air collector. In such cases, gravity or the natural direction of exhaled air is used, such as when the exhaled air hits the exhaled air blocking surface of the exhaled air collector it naturally heads downward to the air suction intake; the air suction intake, in aspects, may also assist downward flow of the exhaled air towards the air suction intake and into, for example, a conduit or air purification chamber.

Figure 17:
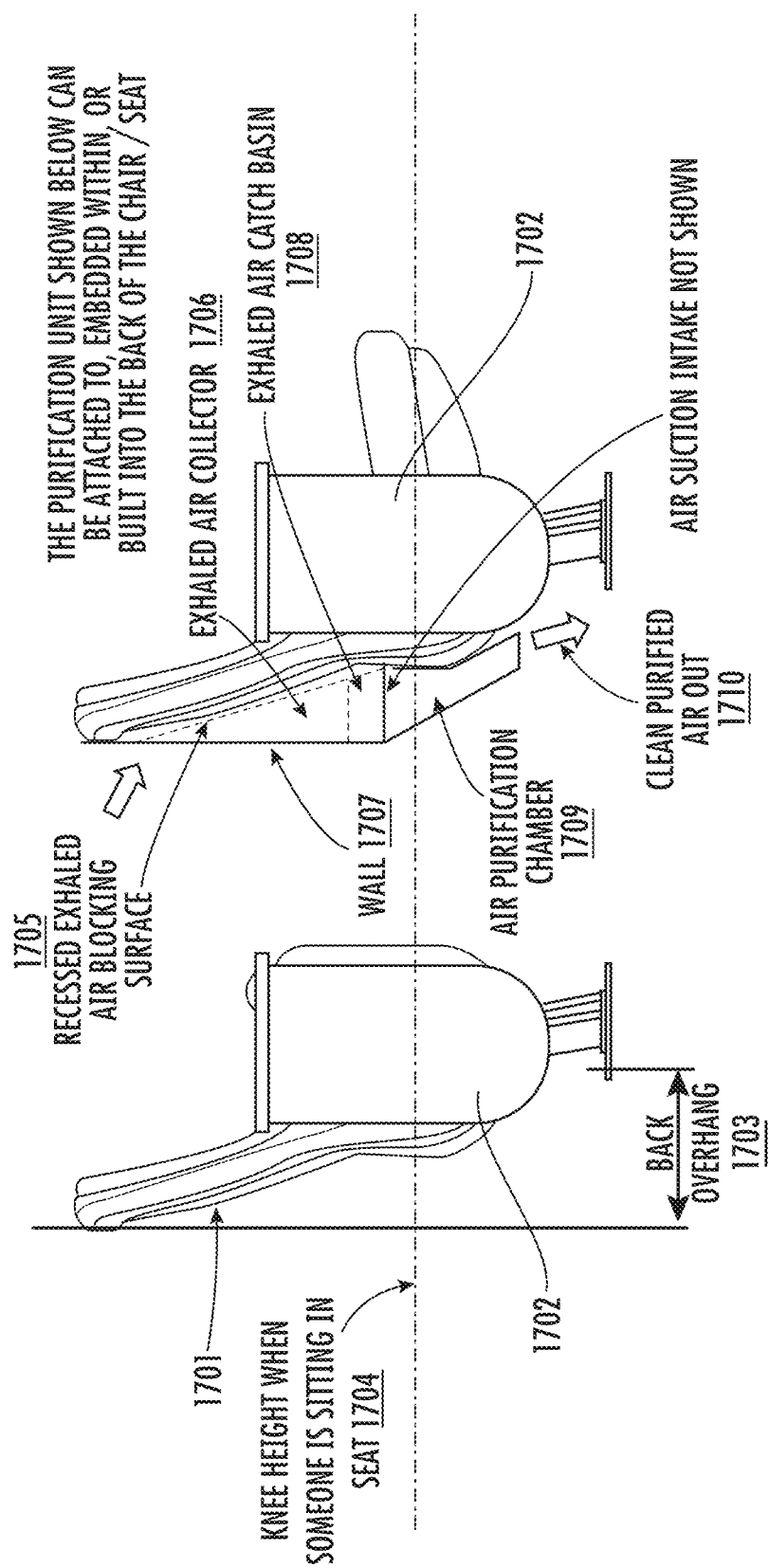
FIG. 17 is a schematic showing aspects of an air purification unit as described herein.

FIG. 17 shows an embodiment of an air purification attached to, embedded or integrated within, or built into the back of a seat 1701. The figure shows a chair 1702 showing a back overhang 1703 and a knee height when somebody is sitting in the seat 1704. This embodiment shows the air purification unit being provided under the overhang of the seat. In this embodiment, the air purification unit comprises a recessed exhaled air blocking surface 1705 recessed within the exhaled air collector 1706 (see wall of air collector 1707). At the bottom of the exhaled air collector is an exhaled air catch basin 1708, wherein typically an air suction aspect would bring exhaled air into the air purification chamber 1709, which, in cases, sends cleaned and/or purified air out 1710.

Figure 18:
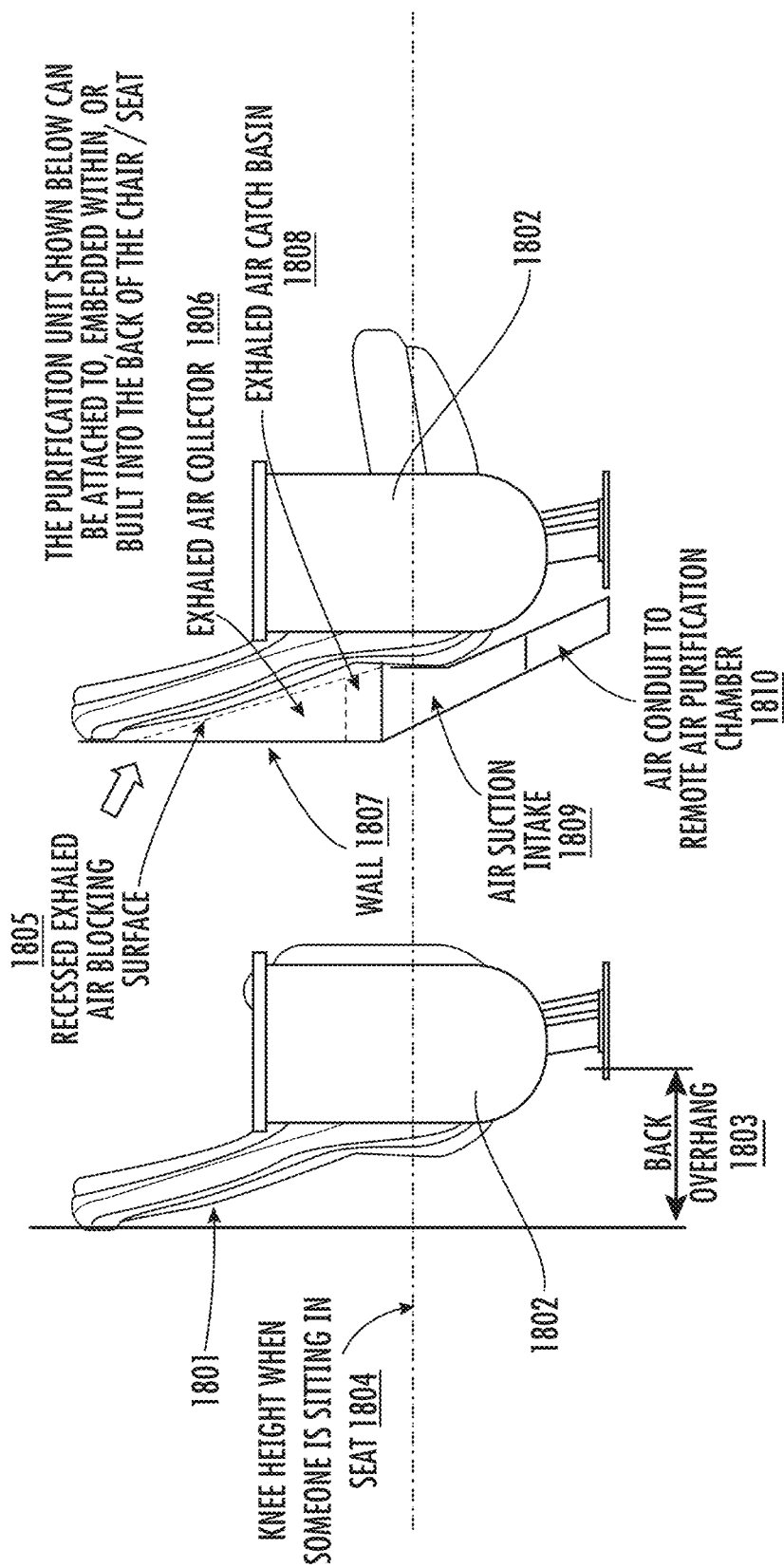
FIG. 18 is schematic showing aspects of an air purification unit as described herein.

FIG. 18 shows an embodiment of an air purification attached to, embedded or integrated within, or built into the back of a seat 1801. The figure shows a chair 1802 showing a back overhang 1803 and a knee height when somebody is sitting in the seat 1804. This embodiment shows the air purification unit being provided under the overhang of the seat. In this embodiment, the air purification unit comprises a recessed exhaled air blocking surface 1805 recessed within the exhaled air collector 1806 (see wall of air collector 1807). At the bottom of the exhaled air collector is an exhaled air catch basin 1808, which, in this case, leads to an air suction intake 1809, which, in this case, sends air to a conduit 1810, which, in aspects, may transport that air to a remote air purification chamber.

Figure 19A:
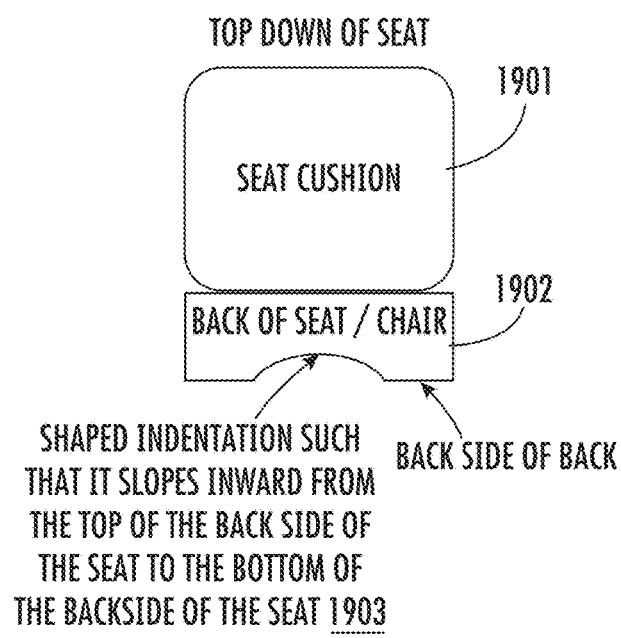
FIGS. 19A and 19B are schematics showing aspects of an air purification unit as described herein.
Figure 19B:
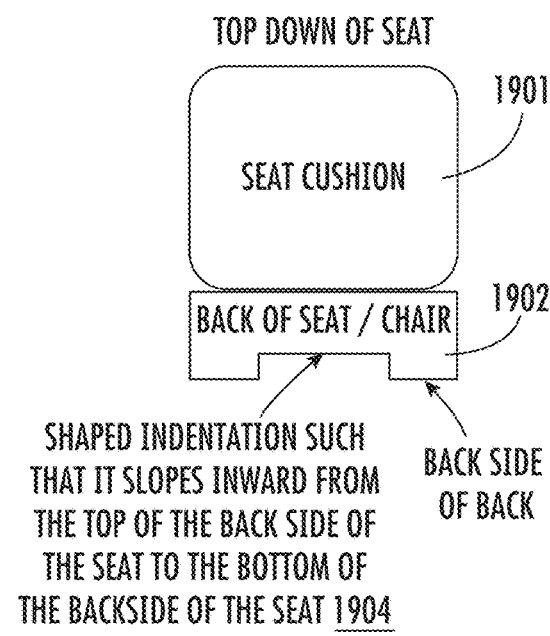
Figure 20A:
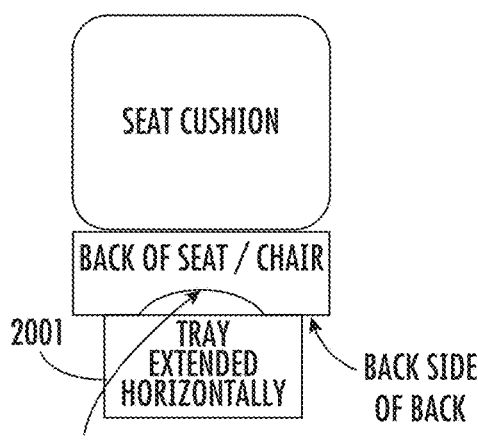
FIGS. 20A and 20B are schematics showing aspects of an air purification unit as described herein.
Figure 20B:
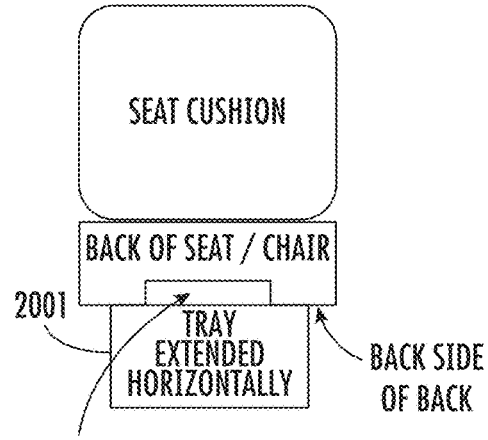
Figure 21A:
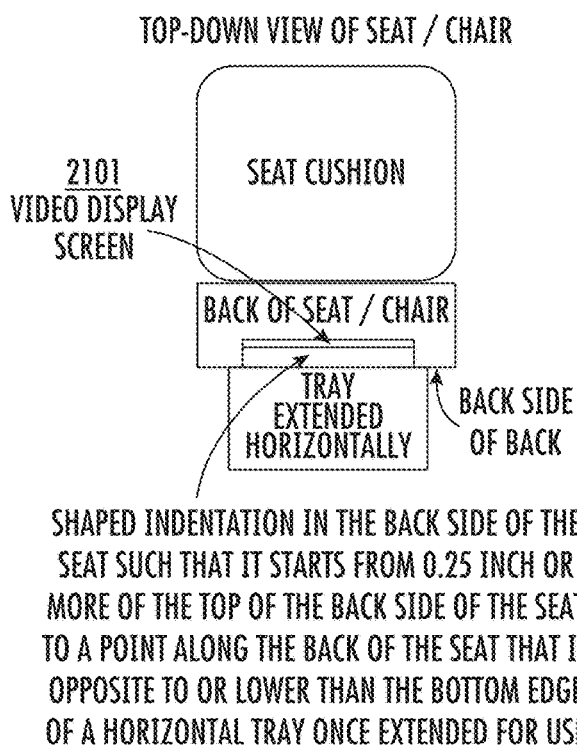
FIGS. 21A and 21B are schematics showing aspects of an air purification unit as described herein.
Figure 21B:
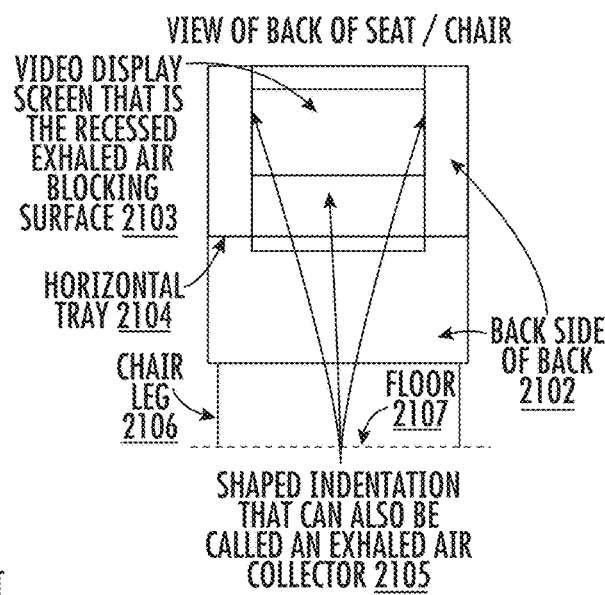
Figure 22A:
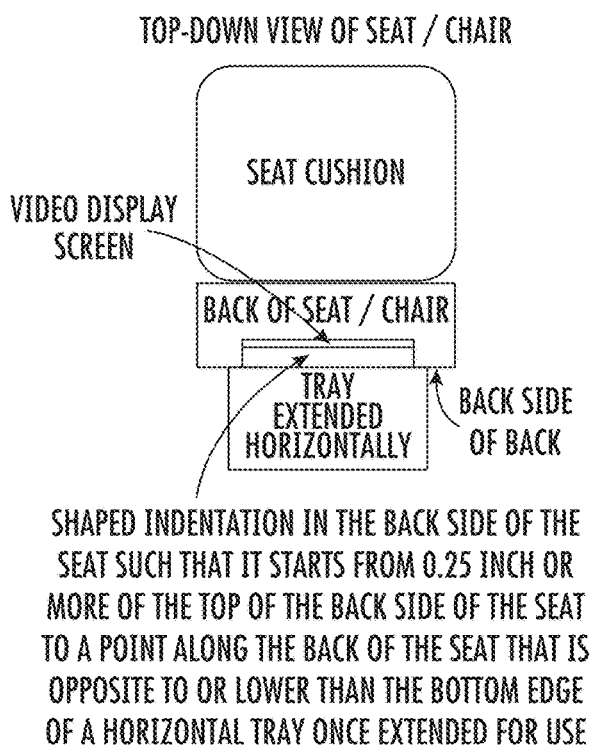
FIGS. 22A and 22B are schematics showing aspects of an air purification unit as described herein.
Figure 22B:
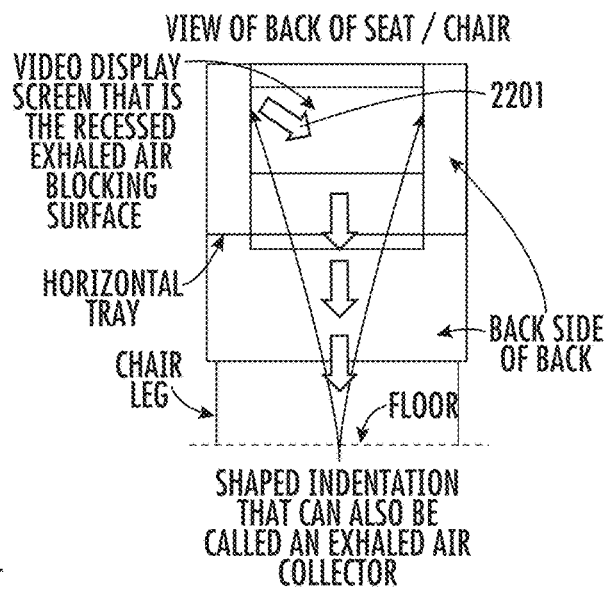
Figure 23A:
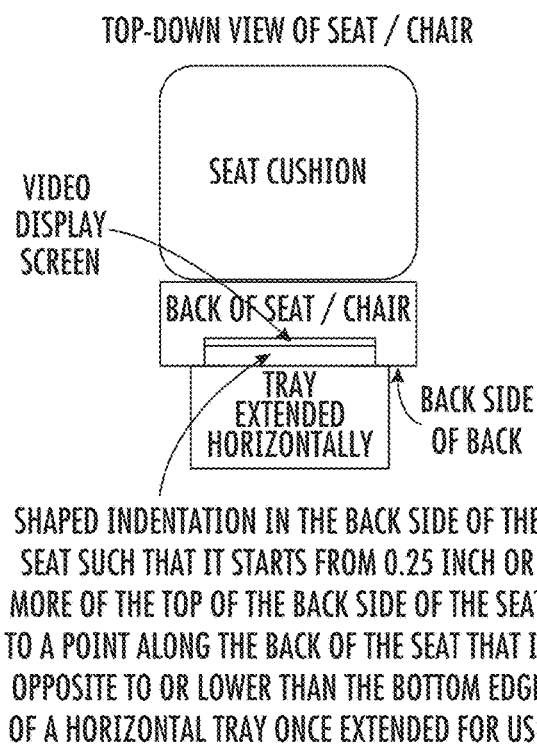
FIGS. 23A and 23B are schematics showing aspects of an air purification unit as described herein.
Figure 23B:
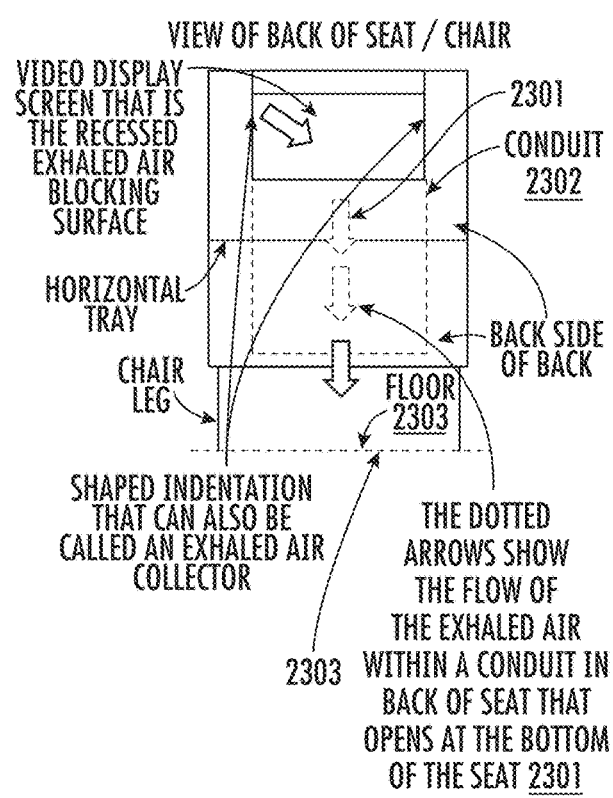
Figures 24A, 24B:
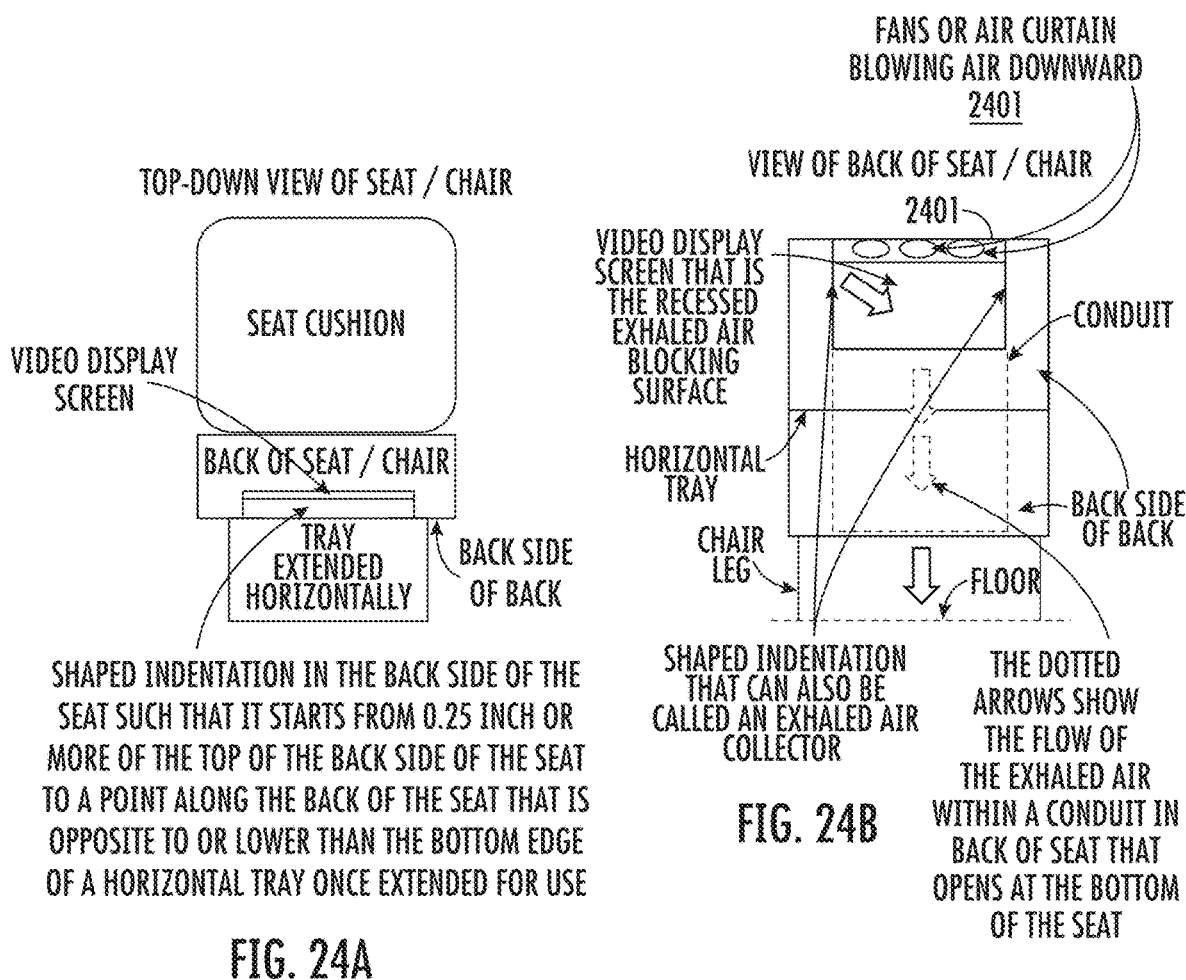
FIGS. 24A and 24B are schematics showing aspects of an air purification unit as described herein.
Figure 27:
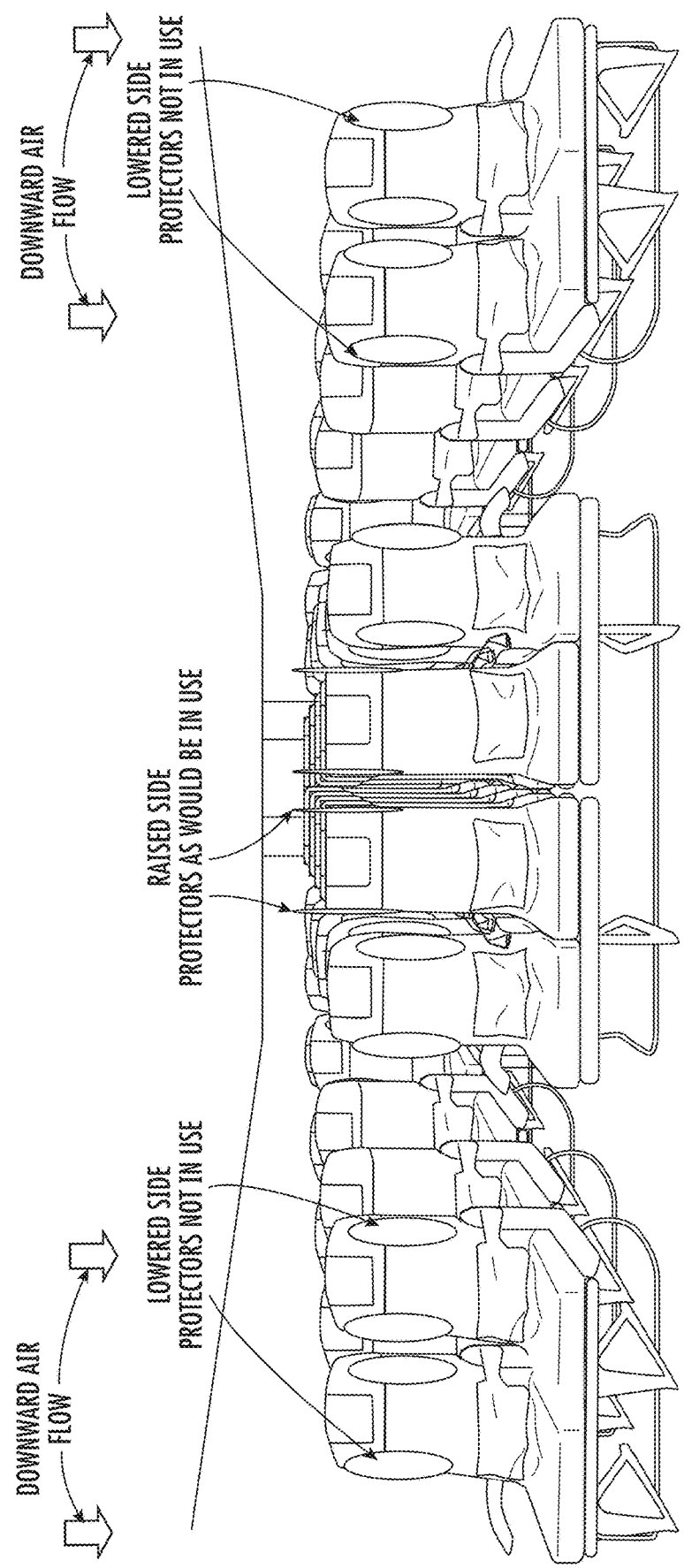
FIG. 27 is a schematic showing aspects of exhaled air protectors as described herein.

FIG. 19A shows the back of a seat shaped to divert exhaled air downwards towards the floor. It shows a seat looking from the top down with a seat cushion 1901 where a passenger sits and the back of the seat 1902 wherein a shaped indentation 1903 slopes inward from the top (or near the top) of the back side of the seat towards the bottom of the back side of the seat. FIG. 19B shows a similar shows a different shaped indentation 1904. FIG. 20 shows similar embodiments wherein a tray is extended horizontally 2001 from the back of the seat, such as a tray table on the back of an aircraft cabin seat. In aspects, the shaped indentation on the back side of the seat starts 0.25 inch or more from the top of the back side of the seat and extends down to a point on or along the back side of the seat that is opposite to or lower than the bottom edge of the horizontal tray, such as when it down and/or extended for use. FIG. 21 shows a similar embodiment but wherein the shaped indentation includes a video display screen 2101. For clarity, a fan or fans can be located at the top of the indentation facing downward in order to blow, direct, or move exhaled air captured by the shaped indentation (e.g., the exhaled air collector) downward towards the floor through, via, or by way of the indentation in the back of the seat. In embodiments, the indentation connects to a conduit within or attached to the back of the seat. FIG. 21B is a view of the back of the seat showing the back side of the back of the seat 2102 and the video display screen 2103 that is, in aspects, the recessed exhaled air blocking surface. FIG. 21B also shows where, in aspects, the horizontal tray 2104 is located relative to the screen and the shaped indentation 2105 that can also, in cases, act as the exhaled air collector. FIG. 21B also shows chair legs 2106 and the floor 2107. In the view of the back side of the seat in FIG. 22, similar to FIG. 21B. FIG. 22 includes arrows 2201 showing a path of exhaled air that contacts the display screen acting as the recessed exhaled air blocking surface and then wherein the exhaled air moves down the exhaled air collector and towards the floor. This movement can be aided, in aspects, by a fan or fans or an air handling system of a vehicle, such as an aircraft, car, bus, truck, or train. In aspects, the movement of the exhaled air happens as gravity pulls the exhaled air downwards. FIG. 23 is similar to FIG. 22 but adds dotted arrows 2201 showing the flow of exhaled air within a conduit 2202 in the back of the seat (or attached to the back of the seat) that opens at the bottom of or near or towards the bottom of the seat (such as at or near the floor 2203). FIG. 24 is similar to FIG. 23 but shows a fan or fans 2401 located at the top of or above the air purification unit or exhaled air collector that blow air downwards, such as providing an air curtain blowing air downwards.

FIG. 25 shows an embodiment of an air purification unit with an attachable or fixed head rest. In this figure, the back of the chair 2501 is shown and the front of the char is shown 2511 along with an air purification unit that hooks onto the top of the chair, such as using a seat top hook attachment 2512, and includes a head rest 2502 for the chair onto which the air purification unit is attached. As elsewhere described herein, the air purification unit is shown with an exhaled air collector 2503 wherein exhaled air 2504 is directed, including a recessed exhaled air blocking surface 2505. The air passes to an air purification chamber 2506, which in this embodiment comprises an optional trap guide 2507 for objects that fall into the chamber and optional UVC lights 2508. This embodiment also shows an optional fan 2509 at or towards the bottom of the air purification unit, which blows clean air 2510 out of the air purification unit.

FIG. 26 shown an embodiment wherein an exhaled air collector 2601 is built into a seat back 2602 and optionally comprises a video screen 2603, which in cases can act as an exhaled air collector blocking surface (which in aspects is recessed into the back of the seat). In this embodiment the air collector leads to an air suction conduit 2604, which is directed towards the bottom of the seat and then out of the environment (e.g., aircraft cabin). The arrows 2605 indicate movement of exhaled air.

Figure 28:
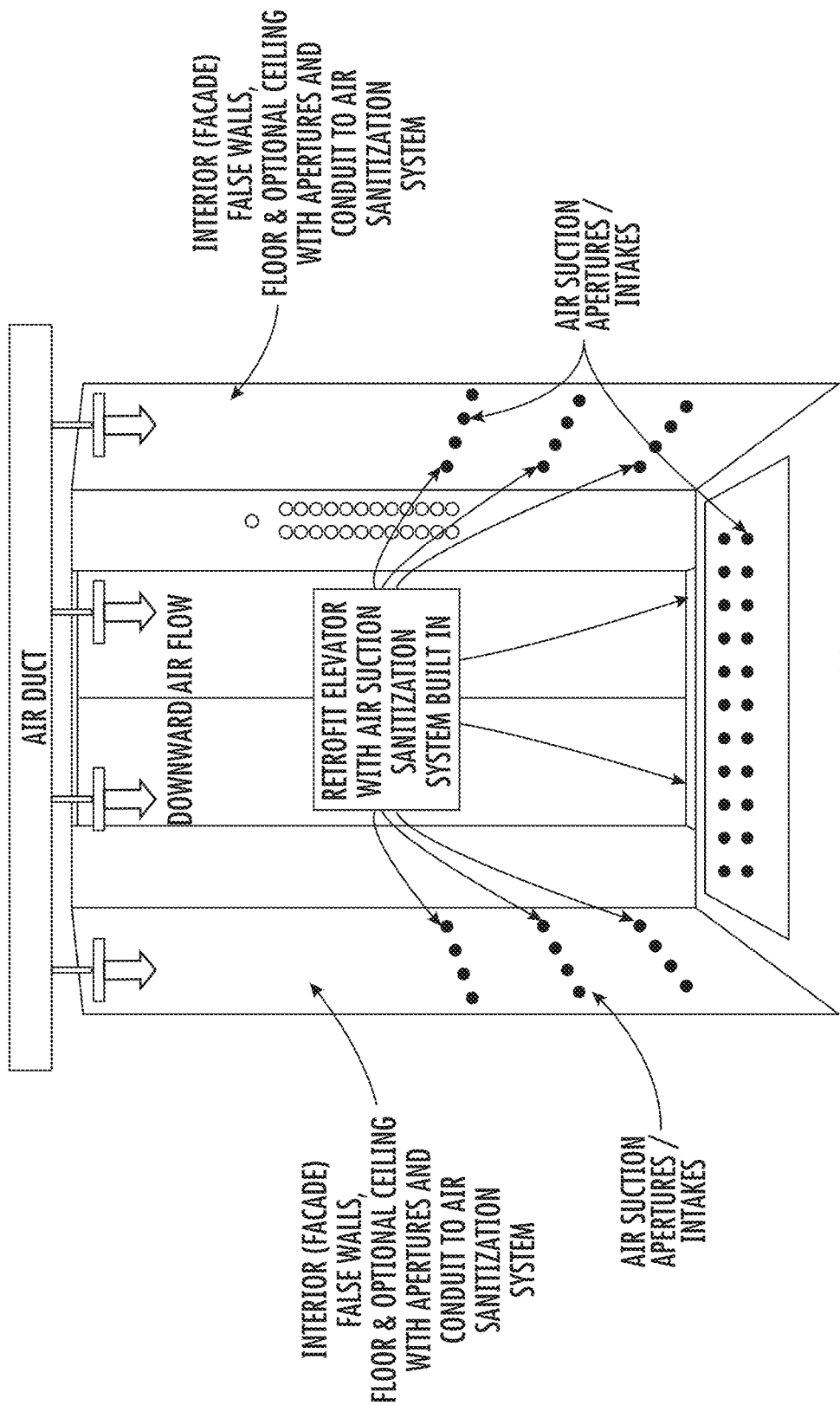
FIG. 28 is a schematic showing aspects of an air purification system as described herein being used to retrofit an elevator car with the air purification system.

FIG. 28 shows an embodiment in an elevator car wherein an elevator car may be retrofitted with an air suction sanitization system. In this aspect, interior (façade) false walls may be used, along with optional floor aspects, comprising apertures connected to conduits that lead to an air sanitization system or unit. In aspects, an air duct leads to vents or nozzles or holes at or near the ceiling that blow air downward, creating a downward air flow. This downward air flow directs exhaled air downwards and towards apertures in the walls and/or floor that in cases suck the air through the apertures into a conduit that may lead to an air purification system, such as an air purification chamber. FIG. 29 shows an embodiment but wherein the elevator car is manufactured with the downward air flow elements and apertures and conduits and does not require retrofitting (e.g., using façades) as shown in FIG. 28.

An embodiment of the invention is:
An air handling device comprising an exhaled air collector and an air suction conduit, wherein the exhaled air collector is connected to the air suction conduit, wherein the air handling device is attached to, incorporated into, connected to, integrated with, part of, and/or separated and located behind a sitting apparatus, wherein the exhaled air collector collects, captures, and/or redirects exhaled air, wherein the air suction conduit transports the exhaled air in a downwards direction towards a floor or a ground, and wherein the air suction conduit comprises an opening that releases the exhaled air above the floor or the ground.

An embodiment of the invention is:
An air handling device comprising an exhaled air collector attached to, incorporated into, connected to, integrated with, part of, and/or separated and located behind a sitting apparatus, wherein the exhaled air collector comprises or is connected to an air suction intake, wherein the air suction intake is connected directly to an air purification chamber or is connected to an air suction conduit that leads to a remote air purification chamber.

An embodiment of the invention blocks and deflects exhaled air >captures and collects exhaled air >releases non-filtered and non-cleaned exhaled air into the venue.

An embodiment of the invention blocks and deflects exhaled air >captures and collects exhaled air >releases non-filtered and non-cleaned exhaled air >the non-filtered and non-cleaned exhaled air is moved by the venue's air flow into one or more of the venue's HVAC system, air purification system, or air handling system.

An embodiment of the invention blocks and deflects exhaled air >captures and collects exhaled air >cleans exhaled air >releases cleaned exhaled air into the venue.

An embodiment of the invention blocks and deflects exhaled air >captures and collects exhaled air >cleans and filters exhaled air >releases cleaned and filtered exhaled air into the venue.

An embodiment of the invention blocks and deflects exhaled air >captures and collects exhaled air >cleans and filters exhaled air >releases the cleaned and filtered exhaled air to the outdoors.

An embodiment of the invention blocks and deflects exhaled air >captures and collects exhaled air >cleans exhaled air >releases the cleaned exhaled air to the outdoors.

An embodiment of the invention blocks and deflects exhaled air >captures and collects exhaled air >cleans and filters exhaled air >moves the cleaned and filtered exhaled air into venue's HVAC system.

An embodiment of the invention blocks and deflects exhaled air >captures and collects exhaled air >moves the exhaled air into one or more of the venue's HVAC system and/or air purification chamber where it is cleaned and/or filtered and moved into the venue by the venue's air handling system.

Embodiments of the invention also include a computer readable medium comprising one or more computer files comprising a set of computer-executable instructions for performing one or more of the calculations, steps, processes, and operations described and/or depicted herein. In exemplary embodiments, the files may be stored contiguously or non-contiguously on the computer-readable medium.

Embodiments may include a computer program product comprising the computer files, either in the form of the computer-readable medium comprising the computer files and, optionally, made available to a consumer through packaging, or alternatively made available to a consumer through electronic distribution. As used in the context of this specification, a "computer-readable medium" is a non-transitory computer-readable medium and includes any kind of computer memory such as floppy disks, conventional hard disks, CD-ROM, Flash ROM, non-volatile ROM, electrically erasable programmable read-only memory (EEPROM), and RAM. In exemplary embodiments, the computer readable medium has a set of instructions stored thereon which, when executed by a processor, cause the processor to perform tasks, based on data stored in the electronic database or memory described herein. The processor may implement this process through any of the procedures discussed in this disclosure or through any equivalent procedure.

In other embodiments of the invention, files comprising the set of computer-executable instructions may be stored in computer-readable memory on a single computer or distributed across multiple computers. A skilled artisan will further appreciate, in light of this disclosure, how the invention can be implemented, in addition to software, using hardware or firmware. As such, as used herein, the operations of the invention can be implemented in a system comprising a combination of software, hardware, or firmware.

Embodiments of this disclosure include one or more computers or devices loaded with a set of the computer-executable instructions described herein. The computers or devices may be a general purpose computer, a special-purpose computer, or other programmable data processing apparatus to produce a particular machine, such that the one or more computers or devices are instructed and configured to carry out the calculations, processes, steps, operations, algorithms, statistical methods, formulas, or computational routines of this disclosure. The computer or device performing the specified calculations, processes, steps, operations, algorithms, statistical methods, formulas, or computational routines of this disclosure may comprise at least one processing element such as a central processing unit (i.e., processor) and a form of computer-readable memory which may include random-access memory (RAM) or read-only memory (ROM). The computer-executable instructions can be embedded in computer hardware or stored in the computer-readable memory such that the computer or device may be directed to perform one or more of the calculations, steps, processes and operations depicted and/or described herein.

Additional embodiments of this disclosure comprise a computer system for carrying out the computer-implemented method of this disclosure. The computer system may comprise a processor for executing the computer-executable instructions, one or more electronic databases containing the data or information described herein, an input/output interface or user interface, and a set of instructions (e.g., software) for carrying out the method. The computer system can include a stand-alone computer, such as a desktop computer, a portable computer, such as a tablet, laptop, PDA, or smartphone, or a set of computers connected through a network including a client-server configuration and one or more database servers. The network may use any suitable network protocol, including IP, UDP, or ICMP, and may be any suitable wired or wireless network including any local area network, wide area network, Internet network, telecommunications network, Wi-Fi enabled network, or Bluetooth enabled network. In one embodiment, the computer system comprises a central computer connected to the internet that has the computer-executable instructions stored in memory that is operably connected to an internal electronic database. The central computer may perform the computer-implemented method based on input and commands received from remote computers through the internet. The central computer may effectively serve as a server and the remote computers may serve as client computers such that the server-client relationship is established, and the client computers issue queries or receive output from the server over a network.

The input/output interfaces may include a graphical user interface (GUI) which may be used in conjunction with the computer-executable code and electronic databases. The graphical user interface may allow a user to perform these tasks through the use of text fields, check boxes, pull-downs, command buttons, and the like. A skilled artisan will appreciate how such graphical features may be implemented for performing the tasks of this disclosure. The user interface may optionally be accessible through a computer connected to the internet. In one embodiment, the user interface is accessible by typing in an internet address through an industry standard web browser and logging into a web page. The user interface may then be operated through a remote computer (client computer) accessing the web page and transmitting queries or receiving output from a server through a network connection.

One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all the references cited in this disclosure are each individually incorporated by reference herein in their entireties and as such are intended to provide an efficient way of supplementing the enabling disclosure of this invention as well as provide background detailing the level of ordinary skill in the art. It is noteworthy that in certain embodiments, the reference to an aircraft is utilized. However, such embodiments can be utilized for all types of vehicles where multiple seated individuals are seated one behind the other. It is noteworthy that in certain embodiments the reference to a theater is utilized. However, such embodiments can be utilized for all types of theaters where multiple seated individuals are seated one behind the other.

As used herein, the term "about" refers to plus or minus 5 units (e.g., percentage) of the stated value.

Reference in the specification to, e.g., "some embodiments," "an embodiment," "one embodiment," or "other embodiments" means that a particular feature, structure, or characteristic described in connection with the embodiments is included in at least some embodiments, but not necessarily all embodiments, of the inventions.

As used herein, the term "substantial" and "substantially" refers to what is easily recognizable to one of ordinary skill in the art.

It is to be understood that the phraseology and terminology employed herein is not to be construed as limiting and are for descriptive purpose only.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

The invention claimed is:

1. An air handling device comprising an exhaled air collector, the exhaled air collector comprising a physical structure having an open front and an exhaled air blocking surface, wherein the exhaled air collector further comprises or connects to an exhaled air catch basin, wherein all or a portion of the exhaled air catch basin is located at the bottom, near the bottom of, or beneath the exhaled air blocking surface, wherein the exhaled air catch basin connects to either a conduit or an exhaled air purification chamber, and wherein the exhaled air collector collects or captures exhaled air in a form of one or more of an exhaled breath, a cough, or a sneeze.

2. The air handing device of claim 1, wherein the exhaled air collector is secured to a chair or supported by a chair.

3. The air handing device of claim 1, wherein the exhaled air blocking surface is an electronic display screen.

4. The air handing device of claim 1, wherein the exhaled air blocking surface is recessed.

5. The air handing device of claim 1, wherein the exhaled air blocking surface is recessed between 0.25 inches and 6 inches.

6. The air handing device of claim 1, wherein the exhaled air purification chamber disperses or exhausts cleaned air into a room from which the exhaled air was captured or collected, and wherein the cleaned air is dispersed or exhausted below the exhaled air blocking surface.

7. The air handing device of claim 1, wherein the exhaled air purification chamber comprises one or more ultraviolet ("UV") light, UVC light, microbicidal energy, microbicidal agent, microbicidal liquid, microbicidal light, microbicidal material, microbicidal components, microbicidal nanoparticles, microbicidal ions, microbicidal heating element, filter, High Efficiency Particulate Air (HEPA) filter, or combinations thereof.

8. The air handing device of claim 1, wherein the exhaled air purification chamber is located at or below knee height of a user whose exhaled air is being captured or collected by the exhaled air collector.

9. The air handing device of claim 1, wherein the exhaled air purification chamber comprises a trap for debris.

10. The air handing device of claim 1, further comprising an air suction intake, wherein the air suction intake is optionally covered with a screen or a grate comprising multiple openings.

11. The air handing device of claim 3, wherein the exhaled air catch basin comprises an air suction intake and is located beneath the electronic display screen.

12. The air handing device of claim 1, wherein the air handling device is mobile or otherwise capable of being moved from one location to another.

13. The air handing device of claim 1, further comprising a carbon dioxide ("$CO_2$") detector.

14. The air handing device of claim 1, wherein part or all of the air handling device is located within one of an indoor multi-seated venue or environment, a building, a theater, an auditorium, an educational venue, a school, a sports venue, an athletic venue, a performing arts venue, a cinema, an opera house, a ballet venue, a music venue, an arena, a house of worship, a church, a synagogue, a temple, a mosque, a vehicle, an automobile, a bus, a train, a boat, an aircraft, an airplane, a jet, a ship, a car, a truck, or a subway.

15. An air handling device comprising an exhaled air collector, the exhaled air collector comprising:
an adjacent or distance removed exhaled air suction intake; and
an open front partially or fully surrounding an exhaled air blocking surface, the exhaled air blocking surface comprising an outer front surface of an electronic display screen, wherein the outer front surface of the electronic display screen deflects or directs exhaled air of a user downwards towards the adjacent or distance removed air suction intake;
wherein the adjacent or distance removed air suction intake moves the exhaled air of the user to or towards an exhaled air purification chamber, and wherein the exhaled air purification chamber releases or exhausts cleaned air into a room where the exhaled air purification chamber is located.

16. The air handling device of claim 15, wherein the exhaled air collector is secured to a chair or supported by a chair.

17. The air handling device of claim 15, wherein the exhaled air blocking surface is recessed.

18. The air handling device of claim 15, wherein the exhaled air purification chamber releases or exhausts the cleaned air into the room below the exhaled air blocking surface.

19. The air handling device of claim 15, wherein the exhaled air purification chamber comprises one or more ultraviolet ("UV") light, UVC light, microbicidal energy, microbicidal agent, microbicidal liquid, microbicidal light, microbicidal material, microbicidal components, microbicidal nanoparticles, microbicidal ions, microbicidal heating element, filter, High Efficiency Particulate Air (HEPA) filter, or combinations thereof.

20. The air handling device of claim 15, wherein the exhaled air purification chamber is located at or below knee height of the user.

21. The air handling device of claim 15, further comprising an exhaled air catch basin.

22. The air handling device of claim 15, wherein the adjacent or distance removed air suction intake is covered with a screen or a grate comprising multiple openings.

23. The air handling device of claim 21, wherein the exhaled air catch basin comprises an air suction intake, and wherein the exhaled air catch basin is located beneath the electronic display screen.

24. The air handling device of claim 15, wherein the air handling device is mobile or otherwise capable of being moved from one location to another.

25. The air handling device of claim 15, wherein part or all of the air handling device is located within one of an indoor multi-seated venue or environment, a building, a theater, an auditorium, an educational venue, a school, a sports venue, an athletic venue, a performing arts venue, a cinema, an opera house, a ballet venue, a music venue, an arena, a house of worship, a church, a synagogue, a temple, a mosque, a vehicle, an automobile, a bus, a train, a boat, an aircraft, an airplane, a jet, a ship, a car, a truck, or a subway.

26. An exhaled air collector comprising an exhaled air blocking surface that blocks exhaled air and room air and deflects or directs the blocked exhaled air and room air towards an exhaled air purification chamber, and wherein the exhaled air blocking surface comprises a front surface of an electronic display screen, a surface formed within a shaped indentation in a back of a chair, or combinations thereof.

27. The exhaled air collector of claim 26, wherein the shaped indentation in the back of the chair comprises an exhaled air blocking surface that is above a knee height of a person sitting behind the back of the chair.

28. The exhaled air collector of claim 26, further comprising an exhaled air catch basin and/or an exhaled air suction conduit, wherein the exhaled air catch basin, the exhaled air suction conduit, the exhaled air purification chamber, or any combinations thereof, are located closer to a floor or a ground than a bottom of the exhaled air blocking surface.

29. The exhaled air collector of claim 26, wherein the indentation in the back of the chair partially or fully houses the electronic display screen.

30. The exhaled air collector of claim 26, wherein the exhaled air purification chamber comprises one or more ultraviolet ("UV") light, UVC light, microbicidal energy, microbicidal agent, microbicidal liquid, microbicidal light, microbicidal material, microbicidal components, microbicidal nanoparticles, microbicidal ions, microbicidal heating element, filter, High Efficiency Particulate Air (HEPA) filter, or combinations thereof.

* * * * *